United States Patent
Goto et al.

(10) Patent No.: US 9,406,121 B2
(45) Date of Patent: Aug. 2, 2016

(54) X-RAY CT APPARATUS AND IMAGE RECONSTRUCTION METHOD

(71) Applicant: HITACHI MEDICAL CORPORATION, Tokyo (JP)

(72) Inventors: Taiga Goto, Tokyo (JP); Hisashi Takahashi, Tokyo (JP); Koichi Hirokawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 0 days.

(21) Appl. No.: 14/372,250

(22) PCT Filed: Mar. 18, 2013

(86) PCT No.: PCT/JP2013/057583
§ 371 (c)(1),
(2) Date: Jul. 15, 2014

(87) PCT Pub. No.: WO2013/161443
PCT Pub. Date: Oct. 31, 2013

(65) Prior Publication Data
US 2015/0093003 A1    Apr. 2, 2015

(30) Foreign Application Priority Data

Apr. 24, 2012  (JP) ................. 2012-098374

(51) Int. Cl.
| | |
|---|---|
| G06T 7/00 | (2006.01) |
| G06T 11/00 | (2006.01) |
| G06T 5/00 | (2006.01) |
| A61B 6/03 | (2006.01) |
| A61B 6/00 | (2006.01) |

(52) U.S. Cl.
CPC .............. *G06T 7/0012* (2013.01); *G06T 5/001* (2013.01); *G06T 11/006* (2013.01); *A61B 6/032* (2013.01); *A61B 6/5205* (2013.01); *G06T 2207/10081* (2013.01); *G06T 2211/412* (2013.01)

(58) Field of Classification Search
None
See application file for complete search history.

(56) References Cited

U.S. PATENT DOCUMENTS

| | | | |
|---|---|---|---|
| 6,842,502 B2 * | 1/2005 | Jaffray ................... | A61B 6/032 378/19 |
| 6,917,663 B2 | 7/2005 | Taguchi et al. | |
| 7,653,224 B2 | 1/2010 | Goto et al. | |
| 7,684,539 B2 | 3/2010 | Goto et al. | |
| 7,933,377 B2 * | 4/2011 | Hsieh ..................... | A61B 6/032 378/15 |
| 8,005,287 B2 * | 8/2011 | Grasruck .............. | G06T 11/006 378/4 |
| 2004/0252806 A1 | 12/2004 | Taguchi et al. | |
| 2006/0165211 A1 | 7/2006 | Goto et al. | |
| 2008/0273778 A1 | 11/2008 | Goto et al. | |
| 2014/0226887 A1 * | 8/2014 | Takahashi ............. | A61B 6/032 382/131 |

FOREIGN PATENT DOCUMENTS

| | | |
|---|---|---|
| JP | 11-9582 | 1/1999 |
| JP | 2004-188163 | 7/2004 |
| JP | 2004-337391 | 12/2004 |
| JP | 2005-7169 | 1/2005 |
| JP | 2007/185358 | 7/2007 |
| WO | WO2005/077278 | 8/2005 |

OTHER PUBLICATIONS

Machine Translation of JP11-9582.*
Dennis L. Parker, "Optimal short scan convolution reconstruction for fanbeam CT", Medical Physics, Mar./Apr. 1982, vol. 9, No. 2.
International Search Resort in PCT/JP2013/057583.

* cited by examiner

Primary Examiner — Michelle Entezari
(74) Attorney, Agent, or Firm — Cooper & Dunham LLP

(57) ABSTRACT

To generate a reconstructed image suitable to characteristics of a bilaterally symmetric site and possible to an appropriate image diagnosis, a computation device: computes a back projection phase width at a rotational center and distance between the rotational center location which is a reference location and a pixel to be reconstructed; according to the distance between the rotational center location and the pixel to be reconstructed, sets a function (f1) changing the back projection phase width; computes a back projection phase width in the pixel to be reconstructed, substituting a value of the distance between the rotational center location and a pixel to be reconstructed in the function (f1); computes a view weighting, on the basis of the back projection phase width in the post-correction pixel to be reconstructed and a slope width of a view weighting function; and reconstructs a CT image, using the view weighting.

15 Claims, 23 Drawing Sheets

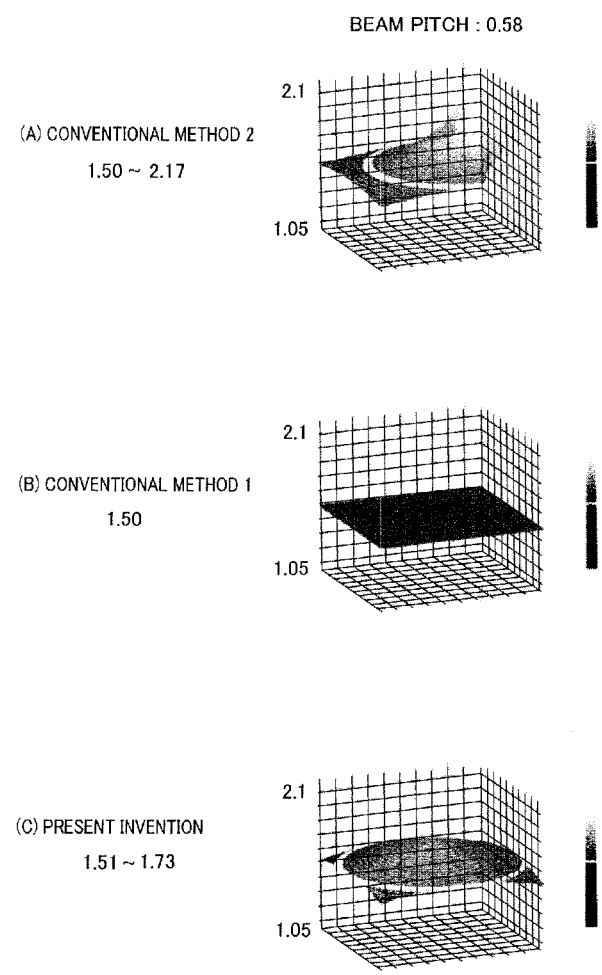

FIG. 21
BEAM PITCH : 0.83
(A) CONVENTIONAL METHOD 2
0.76 ~ 1.32
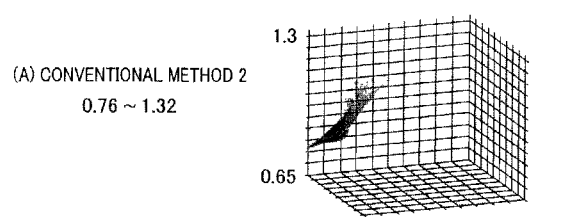
(B) CONVENTIONAL METHOD 1
0.75
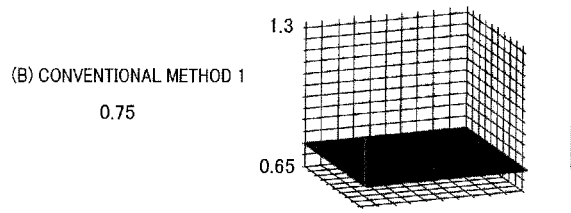
(C) PRESENT INVENTION
0.78-1.20
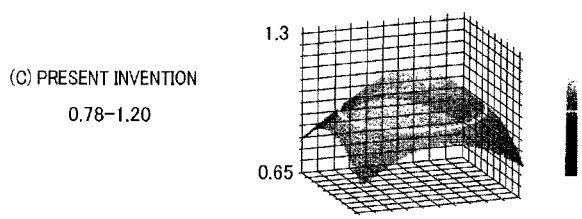

FIG. 22
BEAM PITCH:1.08
(A) CONVENTIONAL METHOD 2
0.62 ~ 1.17
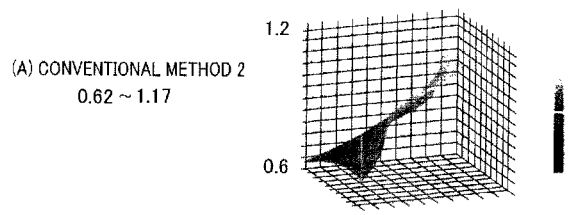
(B) CONVENTIONAL METHOD 1
0.65
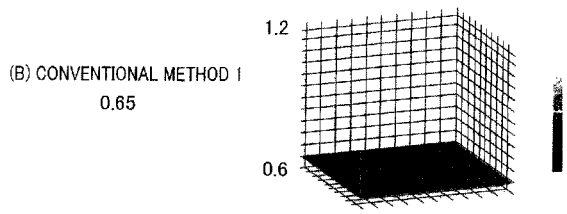
(C) PRESENT INVENTION
0.67 ~ 0.93
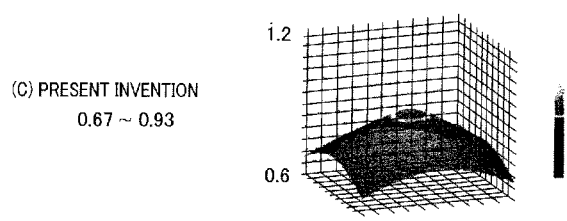

FIG. 24
BEAM PITCH : 0.58
(A) CONVENTIONAL METHOD 2
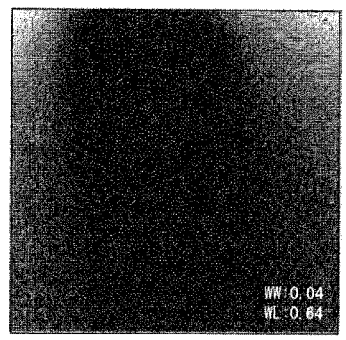
(B) CONVENTIONAL METHOD 1
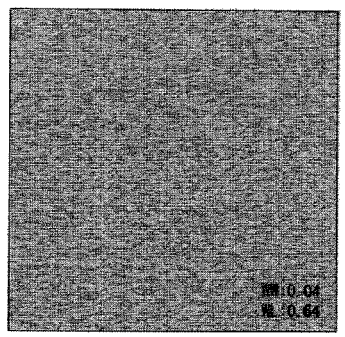
(C) PRESENT INVENTION
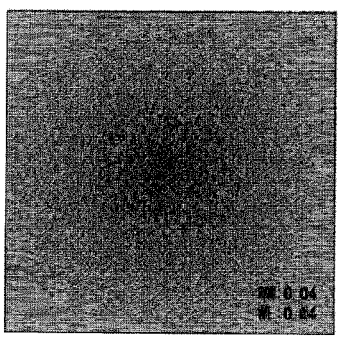

FIG. 25
BEAM PITCH : 0.83
(A) CONVENTIONAL METHOD 2
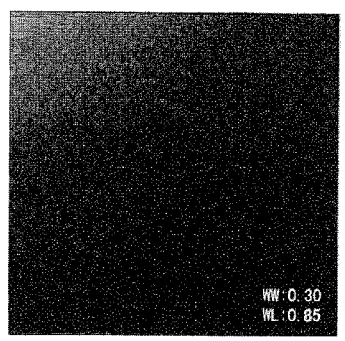
(B) CONVENTIONAL METHOD 1
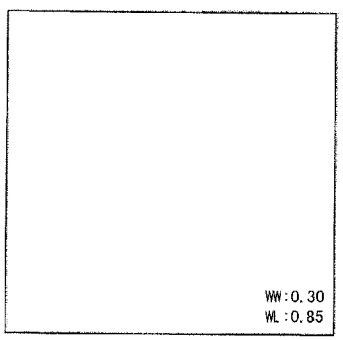
(C) PRESENT INVENTION
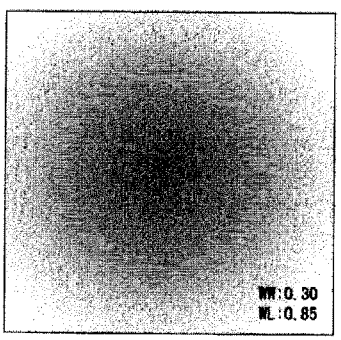

FIG. 26
BEAM PITCH : 1.08
(A) CONVENTIONAL METHOD 2
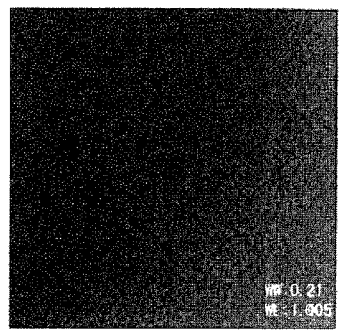
(B) CONVENTIONAL METHOD 1
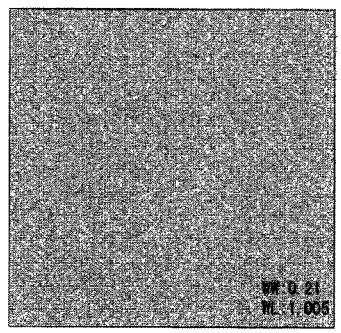
(C) PRESENT INVENTION
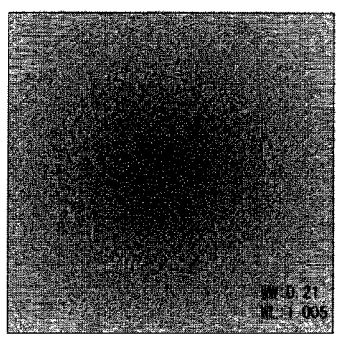

FIG. 27
BEAM PITCH : 1.33
(A) CONVENTIONAL METHOD 2
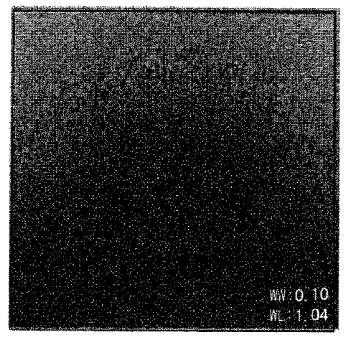
(B) CONVENTIONAL METHOD 1
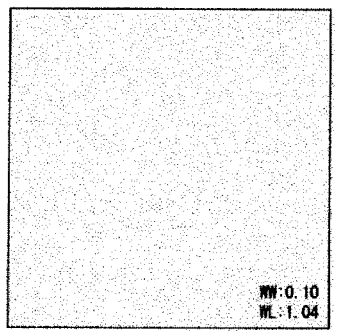
(C) PRESENT INVENTION
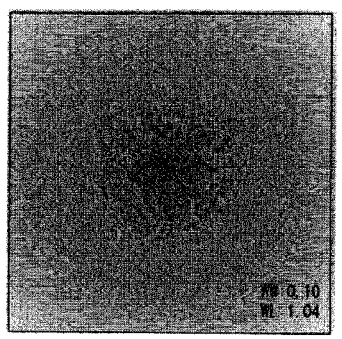

X-RAY CT APPARATUS AND IMAGE RECONSTRUCTION METHOD

TECHNICAL FIELD

The present invention relates to an X-ray CT apparatus and the like that obtain a reconstructed image of a subject in such a manner that an X-ray is irradiated to the subject to measure the X-ray penetrating the subject with an X-ray detector, and pieces of measurement da a from plural directions are reconstructed. In particular, the present invention relates to an X-ray CT apparatus and the like that can control the noise characteristics of the reconstructed image.

BACKGROUND ART

In general, as the angular width (hereinafter, referred to as "back projection phase width") of projection data used for reconstruction is wider, the amount of noise of a reconstructed image is reduced. On the contrary, as the back projection phase width is narrower, the amount of noise of the reconstructed image is increased.

Japanese Patent No. 4360817 discloses a method in which in order to promptly perform a reconstruction process while avoiding noise irregularities in a reconstructed image, an image is reconstructed using the same back projection phase width irrespective of an image position. Specifically, the smallest back projection phase width that can be used in the image is used. As described in Japanese Patent No. 4360817, in the case where a constant back projection phase width is used irrespective of an image position, the amount of noise is stabilized because the back projection phase width becomes a certain value without influence of a reconstruction slice position or an scanning FOV. Further, since the back projection phase width becomes narrower, the temporal resolution becomes higher. On the contrary, in the case where projection data to be used is restricted, the back projection phase width becomes narrower. Thus, the noise is disadvantageously increased as a whole. Further, in the case where the back projection phase width is set wider, an artifact is disadvantageously generated due to extrapolation.

To address such a problem, Japanese Patent No. 4612347 proposes a method in which a weight regulated on the basis of a weight dependent on a cone angle is calculated to be used for back projection, so that more projection data to be reconstructed can be used. In the method of Japanese Patent No. 4612347, more projection data can be used, and thus an image with less noise can be obtained. Further, using the weight dependent on a cone angle, extrapolation errors can be reduced.

SUMMARY OF THE INVENTION

Problem to be Solved by the Invention

However, in the method described in Japanese Patent No. 4612347, the back projection phase width largely differs depending on a position in an image (axial plane). The difference of the back projection phase width causes noise irregularities and temporal resolution irregularities in a reconstructed image.

In particular, in a bilaterally symmetric site such as a breast or a head, generation of noise irregularities on the left and right sides is not desirable from the viewpoint that visibility of a lesion is deteriorated, possibly leading to a misdiagnosis. For example, a head is diagnosed on the basis of a difference between the right and left brains in some cases.

Further, the noise irregularities on an axial image cause generation of striped noise irregularities in an MPR image, and hinder at the time of a diagnosis of a lesion, as similar to the above.

Further, the temporal resolution irregularities cause blurring and a motion artifact to generate a large difference between the left and right sides of a subject who moves. Thus, the temporal resolution irregularities hinder at the time of a diagnosis of a lesion, as similar to the above.

In the case where a constant back projection phase width is used irrespective of an FOV size as in the method of Japanese Patent No. 4360817, the use efficiency of data is relatively low. Thus, the noise of the reconstructed image to be generated is increased, and the exposure dose when a desired image quality is obtained is disadvantageously increased. Further, in the case where a constant back projection phase width in accordance with an FOV size is used in Japanese Patent No. 4360817, the amount of noise and temporal resolution (blurring and a motion artifact caused by motion) are largely changed in accordance with an FOV size in some cases, which is not desirable in diagnosing.

The present invention has been achieved in consideration of the above-described problems, and an object thereof is to provide an X-ray CT apparatus and the like that create a reconstructed image with which a proper image diagnosis in accordance with characteristics of a site (in particular, a bilaterally symmetric site) can be made.

Means for Solving the Problem

In order to achieve the above-described object, a first aspect of the present invention provides an X-ray CT apparatus including: an X-ray generation device that irradiates an X-ray from around a subject; an X-ray detection device that detects the X-ray penetrating the subject; a data collection device that collects data detected by the X-ray detection device; and a computation device that inputs the data collected by the data collection device to create projection data and reconstructs a CT image using the projection data, wherein the computation device calculates a back projection phase width in each pixel on the basis of a distance from a reference position regulated by one or more reference points on an axial plane, calculates a view weight using the back projection phase width in each pixel, and reconstructs the CT image using the view weight.

A second aspect of the present invention provides an image reconstruction method in which provided are: an X-ray generation device that irradiates an X-ray from around a subject; an X-ray detection device that detects the X-ray penetrating the subject; a data collection device that collects data detected by the X-ray detection device; and a computation device that inputs the data collected by the data collection device to create projection data and reconstructs a CT image using the projection data, wherein the computation device calculates a back projection phase width in each pixel on the basis of a distance from a reference position regulated by one or more reference points on an axial plane, calculates a view weight using the back projection phase width in each pixel, and reconstructs the CT image using the view weight.

Advantageous Effect of the Invention

According to the present invention, it is possible to provide an X-ray CT apparatus and the like that create a reconstructed image with which a proper image diagnosis in accordance with characteristics of a site (in particular, a bilaterally symmetric site) can be made.

BRIEF DESCRIPTION OF THE DRAWINGS

FIG. 20 show calculation results of the back projection phase widths in the case of a beam pitch of 0.58.

FIG. 21 show calculation results of the back projection phase widths in the case of a beam pitch of 0.83.

FIG. 22 show calculation results of the back projection phase widths in the case of a beam pitch of 1.08.

FIG. 24 show noise distribution of axial images in the case of a beam pitch of 0.58.

FIG. 25 show noise distribution of the axial images in the case of a beam pitch of 0.83.

FIG. 26 show noise distribution of the axial images in the case of a beam pitch of 1.08.

FIG. 27 show noise distribution of the axial images in the case of a beam pitch of 1.33.

BEST MODE FOR CARRYING OUT THE INVENTION

Figure 1:
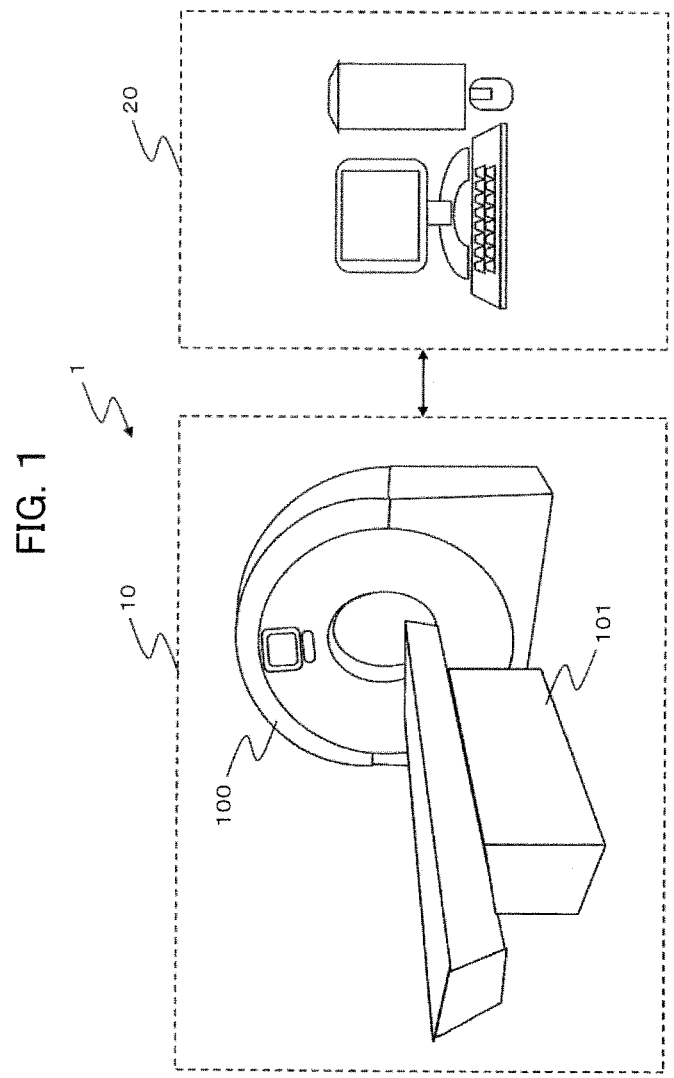
FIG. 1 is a diagram for showing an entire configuration of an X-ray CT apparatus.
Figure 2:
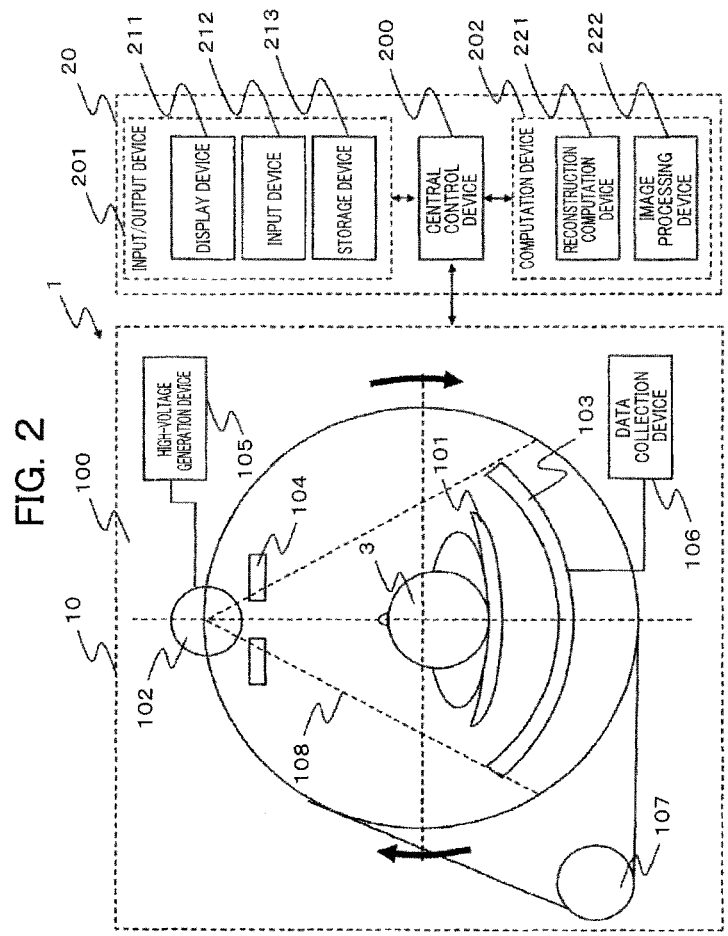
FIG. 2 is a diagram for showing constitutional elements of the X-ray CT apparatus.

Hereinafter, an embodiment of the present invention will be described in detail on the basis of the drawings. First, a configuration of an X-ray CT apparatus 1 will be described with reference to FIG. 1 and FIG. 2.

The X-ray CT apparatus 1 is roughly configured using a scanner 10 and an operation unit 20. The scanner 10 includes a bed device 101, an X-ray generation device 102, an X-ray detection device 103, a collimator device 104, a high-voltage generation device 105, a data collection device 106, a driving device 107, and the like. The operation unit 20 includes a central control device 200, an input/output device 201, a computation device 202, and the like.

An operator inputs scanning conditions, reconstruction conditions, and the like through the input/output device 201. The scanning conditions are, for example, a bed feeding speed, tube current, tube voltage, an scanning range (a range of a slice position), the number of scanning views per rotation, and the like. Further, the reconstruction conditions are, for example, an area of interest, the size of a CT image (the magnitude of a CT image), a reconstruction filter function, and the like. The input/output device 201 includes a display device 211 that displays a CT image and the like, an input device 212 such as a mouse, a trackball, a keyboard, and a touch panel, and a storage device 213 that stores data.

The central control device 200 inputs the scanning conditions and the reconstruction conditions, and transmits a control signal necessary for scanning to each device included in the scanner 10. The collimator device 104 controls the position of a collimator on the basis of the control signal. When the scanning is started in response to an scanning start signal, the high-voltage generation device 105 applies tube voltage and tube current to the X-ray generation device 102 on the basis of the control signal. The X-ray generation device 102 allows a cathode to emit electrons of energy in accordance with the applied tube voltage, and the emitted electrons hit a target (anode), so that an X-ray 108 of energy in accordance with the electron energy is irradiated onto a subject 3.

The driving device 107 allows a gantry 00 on which the X-ray generation device 102, the X-ray detection device 103, and the like are mounted to be rotated around the subject 3 on the basis of the control signal. The bed device 101 controls the bed on the basis of the control signal.

The irradiation area of the X-ray 108 irradiated from the X-ray generation device 102 is limited by the collimator, and the X-ray 108 is absorbed (attenuated) in each tissue of the subject 3 in accordance with an X-ray attenuation coefficient. Then, the X-ray 108 passes through the subject 3, and is detected by the X-ray detection device 103 that is arranged at a position opposed to the X-ray generation device 102.

The X-ray detection device 103 has single-row detectors configured using plural detection elements arranged in the one-dimensional direction (the channel direction) and multi-row detectors configured using plural detection elements arranged in the two-dimensional directions (the channel direction and the row direction orthogonal to the channel direction). In the channel direction, the detection elements are arranged in an arc-like shape in the rotational direction. The multi-row detectors are formed by arranging the single-row detectors in plural rows in the rotational axis direction, and can image a range wider than the single-row detectors at a time.

The X-ray 108 detected by each detection element is converted into low data. Specifically, various data processes (conversion to digital data, LOG conversion, calibration, and the like) are performed by the data collection device 106 for the X-ray 108 detected by the X-ray detection device 103, and the X-ray 108 is input to the computation device 202 as low data.

In this case, the X-ray generation device 102 and the X-ray detection device 103 that are opposed to each other are revolved around the subject 3 (however, excluding positioning scanning), and thus the X-ray generation device 102 irradiates the X-ray 108 from around the subject 3. Further, the X-ray detection device 103 detects the X-ray 108 passing through the subject 3. Specifically, the low data is collected at discrete positions of the X-ray tubes (namely, the opposed positions of the detectors) in the revolution direction. The low data is obtained in a unit of "view" at each position of the X-ray tubes.

The X-ray CT apparatus 1 is roughly separated into a multi-slice CT using the X-ray detection device 103 in which the detection elements are aligned in the two-dimensional directions and a single-slice CT using the X-ray detection device 103 in which the detection elements are aligned in one row, namely, one-dimensional direction (only the channel direction). The multi-slice CT irradiates the X-ray 108 spread in a conical shape or a pyramid shape from the X-ray generation device 102 that is an X-ray source in accordance with the X-ray detection device 103. The single-slice CT irradiates the X-ray 108 spread in a fan shape from the X-ray generation device 102. In general, when scanning with the X-ray CT apparatus 1, the X-ray 108 is irradiated (however, excluding positioning scanning) while the gantry 100 is rotated around the subject 3 placed on the bed.

In spiral scanning, a distance by which the bed is advanced relative to an scanning system during one revolution of the scanning system is defined as "bed moving speed" (mm/revolution). Further, as an index representing scanning performance in the spiral scanning, a ratio of the distance by which the bed is advanced relative to the scanning system during one revolution of the scanning system to the width of the detection element in the rotational axis direction at the rotational axis position of the detection element is defined as "spiral pitch". Further, as another index representing scanning performance, a ratio of the distance by which the bed is advanced relative to the scanning system during one revolution of the scanning system to the entire length of the detection element in the rotational axis direction is defined as "beam pitch".

As the spiral pitch or the beam bitch is larger, the same range can be imaged in the rotational axis direction in a short period of time. The range of an angle at which the subject is imaged at a certain position becomes shorter, and a back projection phase width (angular width of projection data used for reconstruction) becomes narrower.

About 1000 images are generally taken per rotation in the rotational direction by the X-ray CT apparatus 1.

One scanning in the rotational direction is referred to as a unit of "one view". An scanning method in which the bed is fixed during scanning and the X-ray generation device 102 is rotated around the subject 3 in a circular orbit manner is referred to as axial scanning, normal scanning, conventional scanning, or the like (hereinafter, unified to "axial scanning"). In particular, an scanning method in which the subject is imaged by fixing the bed and the scanning is repeated by moving the bed to the next scanning position is referred to as step and shoot scanning. Further, an scanning method in which the bed is continuously moved and the X-ray generation device 102 is rotated around the subject 3 in a spiral orbit manner is referred to as spiral scanning, helical scanning, or the like (hereinafter, unified to "spiral scanning").

In the case of the step and shoot scanning, the bed device 101 allows the bed to stop during scanning. Further, in the case of the spiral scanning, the bed device 101 moves the bed in parallel with the body axis direction of the subject 3 during scanning in accordance with the bed feeding speed that is one of the scanning conditions.

In the case where the subject was imaged by the axial scanning, an image at the position of the X-ray generation device 102 (X-ray source) can be accurately reproduced by performing a filtered two-dimensional back projection. However, in the case where the subject was imaged by the spiral scanning, discontinuousness of data in the phase of an imaged end portion causes a streak-like artifact at a position where the discontinuousness is generated only by the filtered two-dimensional back projection, as similar to the case in which the subject is moved. Accordingly, data interpolation is used for data obtained by the spiral scanning, so that the data is corrected to circular orbit data, and then the filtered two-dimensional back projection is performed. By using the interpolation in such a manner, an image with the discontinuousness reduced can be obtained. The degree of the artifact in this case is dependent on the degree of the discontinuousness in the X-ray source orbit. Specifically, the degree of the artifact is changed depending on the moving speed of the subject.

The computation device 202 is configured using a reconstruction computation device 221, an image processing device 222, and the like. Further, the input/output device 201 is configured using the input device 212, the display device 211, the storage device 213, and the like.

The reconstruction computation device 221 creates projection data by inputting the low data collected by the data collection device, and reconstructs an image using the projection data to generate a CT image.

The reconstruction computation device 221 stores the CT image in the storage device 213. Further, the reconstruction computation device 221 displays the CT image on the display device 211. Alternatively, the image processing device 222 processes the CT image stored in the storage device 213, and displays the processed image on the display device 211.

As reconstruction methods in the multi-slice CT, a method called "feldkamp reconstruction method" obtained by extending a two-dimensional reconstruction method used in the single-slice CT, or a method obtained by applying the feldkamp method is mainly used. In the feldkamp method, the beam inclination of the X-ray 108 in the body axis direction is accurately handled for data obtained by the multi-slice CT, and projection values are assigned to pixels along the route of the beam. Therefore, projection data in the range of the angle at which the X-ray 108 is irradiated to each pixel can be used for back projection.

The reconstruction methods can be classified into reconstruction in which 180-degree data (half scanned data) is used in accordance with the back projection phase width converted to parallel beams to be used, reconstruction in which 180 to 360-degree data (extended half scanned data) is used, reconstruction in which 360-degree data (full scanned data) is used, and reconstruction in which 360 or larger-degree data (over scanned data) is used.

Among these methods, in the reconstruction in which the half scanned data is used, the number of components of the projection data to be used in the time direction is small, and temporal resolution becomes high. However, noise is relatively increased because an image is generated using the minimum projection data. Further, there is no redundancy of the projection data, and thus the artifact is generated sensitive to the motion of the subject.

On the other hand, in the reconstruction in which the over scanned data is used, the temporal resolution is deteriorated. On the contrary, due to the use of more data, an image with less noise can be obtained even in the case of scanning with low tube current.

In the image reconstruction method of the embodiment, the equations for reconstruction in a conventional technique as shown below can be used.

Example of fan beam reconstruction $$I(x, y, z) = \frac{1}{\pi} \int_{\beta_1(x,y,z)}^{\beta_2(x,y,z)} \frac{1}{L^2(\beta, x, y, z)} \int_{\alpha_m}^{\alpha_m} W_f(\beta, \alpha', x, y) \cdot P_f(\beta, \alpha', \upsilon) \cdot g(\alpha - \alpha', \upsilon) \cdot d\alpha' \cdot d\beta \quad (1)$$

wherein I represents image data; x, y, and z, a position (mm) of a pixel to be reconstructed; L, a distance (mm) from the X-ray generation device 102 (X-ray source) to the pixel to be reconstructed; $\beta$, a projection angle (rad) of the fan beam; $W_f(\cdot)$, a view weight for the fan beam; $\alpha$, a fan angle (rad); $P_f(\cdot)$, projection data; $\upsilon$, a detector array position (mm); and $g(\cdot)$, a reconstruction filter.

Example of parallel beam reconstruction $$I(x, y, z) = \frac{1}{\pi} \int_{\phi_1(x,y,z)}^{\phi_2(x,y,z)} \int_{-\infty}^{\infty} W_p(\phi, R) \cdot P_p(\phi, t', \upsilon) \cdot g(t - t') \cdot dt' \cdot d\phi \quad (2)$$

wherein I represents image data; x, y, and z, a position (mm) of a pixel to be reconstructed; $W_p(\cdot)$, a view weight for the parallel beam; $\emptyset$, a projection angle (rad) of the parallel beam; $P_p(\cdot)$ projection data; t, a parallel beam channel position (mm) $\upsilon$, a detector array position (mm); and $g(\cdot)$, a reconstruction filter.

The back projection phase width used for reconstruction may differ depending on each reconstruction pixel, or may be the same. Hereinafter, a case in which the back projection phase width differs depending on each pixel will be described.

Next, problems in the conventional technique will be described with reference to FIG. 3 to FIG. 6.

When scanning the subject, the subject is ideally in an immobile state so as not to generate inconsistency of data. However, in the case where the subject is a human, inconsistency of data is generated under the influence of heart beats, breathing, and blood flow. In particular, the influence of breathing is significant. Thus, when scanning a site influenced by breathing, the breath is generally held during the scanning. It is obvious that there is a time limit to breath holding, and it is impossible for a living person to infinitely hold the breath. Accordingly, it is necessary to image an scanning range in a short period of time to reduce the burden on the subject.

In this case, the influence on an image by the inconsistency of data significantly appears in particular as discontinuity between the scanning start phase and the scanning completion phase of the projection data that is obtained by scanning of one revolution and is supposed to be continuous. It is assumed that the subject is not moved at the time of scanning and scanning on a circular orbit is performed. In this case, for example, there is almost no discontinuity between the scanning start phase and the scanning completion phase of full scanned data in which the imaged back projection phase angular width is $2\pi$. In other words, in an ideal state of the axial scanning, the projection data at the scanning start phase matches that at the scanning completion phase, and the projection data becomes continuous in the phase direction. However, the influence of the motion of a heart and the motion of blood (in particular, a contrast agent) cannot be completely eliminated. If the discontinuity between the scanning start phase and the scanning completion phase becomes large, the image quality is significantly deteriorated such as a streak artifact.

In the case of continuous data that is not discretized in the axial scanning (scanning in a scanning range of $2\pi$) in the fan beam CT, projection data obtained using a beam irradiated from each phase matches that ("line integral" in mathematics) irradiated from the opposed phase. In other words, it is equal to a case in which the subject is imaged twice with the beam orbit of the same X-ray 108 in each phase during one revolution. Here, in the case of reconstructing using the projection data in a range of $2\pi$, the same data is used twice. Thus, this case is assumed as that the redundancy (the number of times of measurements) of data is "2". In the case where the redundancy of data is "1", it means scanning in a scanning range of $2\pi$ or smaller.

A minimum scanning range of $2\pi$ or smaller in which the redundancy of data is "1" can be represented as $\pi+2\alpha(\alpha \leq \pi/2)$. However, if projection data (half scanned data) that can be obtained in a scanning range of $\pi+2\alpha$ is reconstructed as similar to the case of a scanning range of $2\pi$ without consideration of the redundancy of data, the image quality is likely to be deteriorated. This is because an image that can be finally obtained is distorted by the effect of redundant data that differs depending on the rotational phase.

The reason of deterioration of the image quality will be concretely described. For example, in the case where the back projection is performed using data obtained in such a manner that a radiation source is revolved by $\pi+2\alpha$ phases, a data phase range in which the back projection can be performed differs depending on each reconstruction pixel, and an image that can be finally obtained is distorted. This is because in the case of a pixel a, data in a phase range of $\pi$ or larger around the image a is obtained. However, in the case of another pixel b, only data in a phase range of n around the pixel b is obtained.

In the case of scanning with the multi-slice CT, a period of time in which the X-ray 108 is irradiated differs depending on each image position as shown in FIG. 3. Each of FIG. 3 shows a state in which the X-ray 108 is irradiated by the X-ray generation device 102 revolving around the bed that advances rightward along a rotational axis 301. $S(\cdot)$ represents the phase of the projection data. For example, the X-ray generation device 102 irradiates the X-ray 108 from one position of a phase $S(\pi)$ in an area 302, and thus the redundancy (the number of times of measurements) of data is "1". On the other hand, the X-ray generation device 102 irradiates the X-ray 108 from two positions of phases $S(\pi)$ and $S(2\pi)$ in an area 303, and thus the redundancy (the number of times of measurements) of data is "2".

Figure 3A:
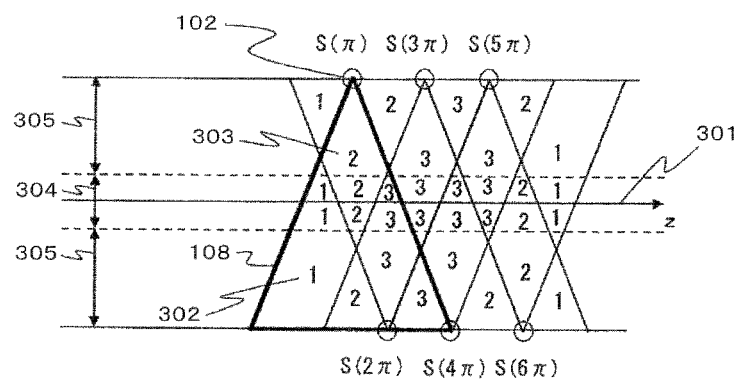
FIG. 3 are diagrams each showing redundancy of measurement.
Figure 3B:
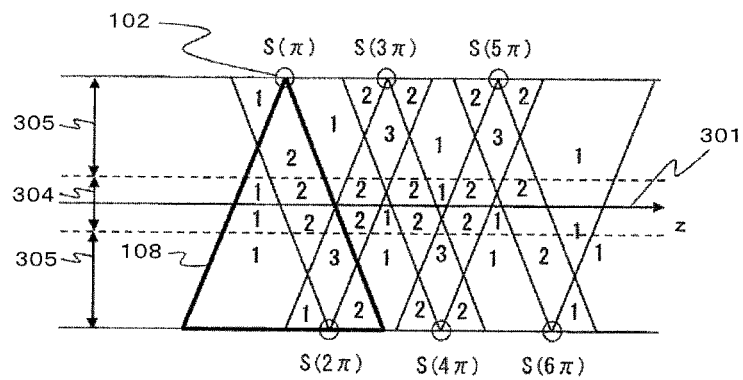

FIG. 3A shows a case in which the bed moving speed is slow. FIG. 3B shows a case in which the bed moving speed is fast. As being apparent from FIG. 3, a period of time (a rotational angular width in which the pixel position is imaged) in which the X-ray 108 is irradiated becomes long at a rotational center position 304 as compared to a position 305 apart from the revolution center (rotational center). In other words, projection data that can be used for reconstruction s collected across plural angular widths at the revolution center position 304. On the other hand, projection data that can be used for reconstruction is collected only across small angular widths at the position 305 apart from the revolution center. Namely, the back projection phase width has extremely high non-linearity relative to the pixel position. Further, as being apparent from FIG. 3A and FIG. 3B by comparison, the back projection phase width has extremely high non-linearity in relation to the bed moving speed.

In order to solve the problems related to the redundant data as described above, Non-patent document 1 (Dennis L. Parker: Optimal shortscan convolution reconstruction for fanbeam CT: Med. Phys., 9, 254-257, 1982) discloses a method to solve using a weighting function. Specifically, for example, when projection data that can be obtained in a scanning range of $2\pi$ is reconstructed, the weighting function disclosed in Non-patent document 1 (Dennis L. Parker: Optimal shortscan convolution reconstruction for fanbeam CT: Med. Phys., 9, 254-257, 1982) is required to satisfy the following equation.

$$W(\beta,\alpha)+W(\pi+\beta+2\alpha,-\alpha)=1 \quad (3)$$

wherein $W(\cdot)$ represents a weighting function; $\beta$, a fan beam projection angle; and $\alpha$, a fan angle.

Figure 4:
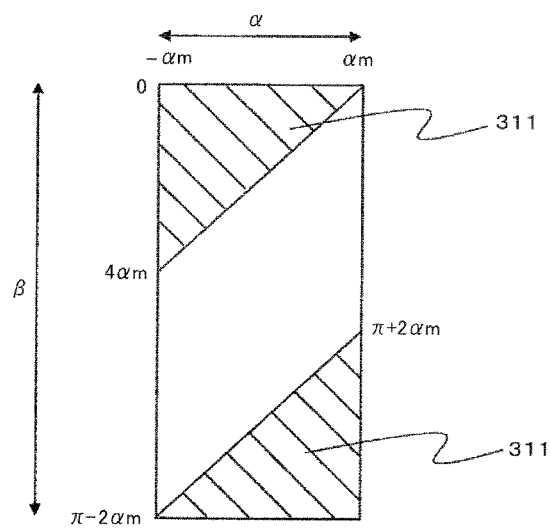
FIG. 4 is a sinogram for showing a minimum complete data set.

FIG. 4 is a sinogram for showing a minimum complete data set. The sinogram is a map in which the horizontal axis represents a fan angle $\alpha$ and the vertical axis represents a fan beam projection angle $\beta$. The redundancy is corrected for an area 311 in FIG. 4 by providing a view weight satisfying the equation (3).

Figure 5:
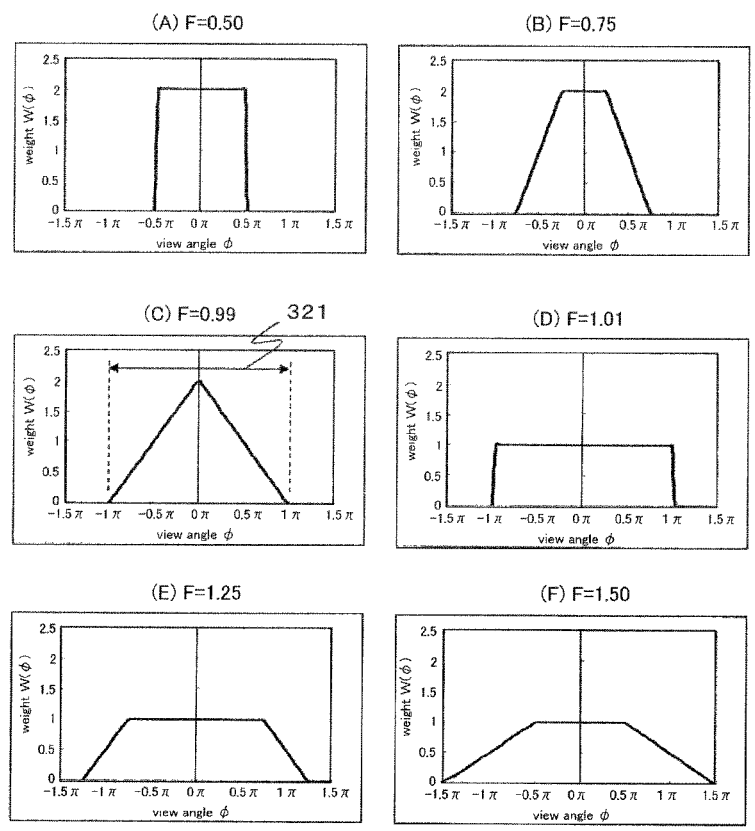
FIG. 5 are diagrams each showing the shape of a view weighting function in a conventional technique.

FIG. 5 are diagrams each showing the shape of a conventional view weighting function. As an example, a back projection phase width $2\pi F$ (rad) is represented by a line 321 in FIG. 5C. In a view weighting function used for conventional image reconstruction, the sum of weights of the back projection phase and the opposed phase is constant as shown in the equation (3), as the necessary and sufficient condition. As the Parker weight described in Non-patent document 1 (Dennis L. Parker: Optimal shortscan convolution reconstruction for fanbeam CT: Med. Phys., 9, 254-257, 1982), when paying attention to some pixel, a general weight shape is a rectangular shape, a trapezoidal shape, or a triangle shape in the view direction, or a non-linear shape thereof in accordance with the back projection phase width $2\pi F$ [rad] as shown in FIG. 5. In this case, the relative amount of image noise that can be obtained for the view weight shape can be represented as shown by the following equation.

$$SD \propto \frac{\sum_{i}^{N_{view}} W(i)^2}{\sum_{i}^{N_{view}} W(i)} \quad (4)$$

wherein SD represents the relative amount of image noise; $W(\cdot)$, a weighting function; and $N_{view}$, the number of imaged views per rotation.

Figure 6:
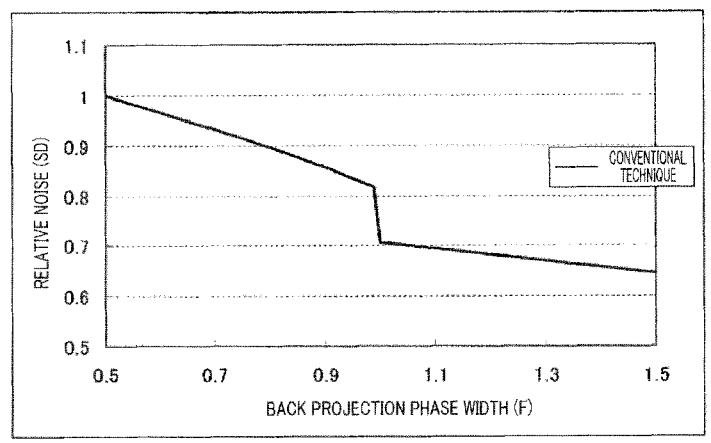
FIG. 6 is a diagram for showing a relation between a back projection phase width and image noise in a view weight of the conventional technique.

FIG. 6 shows a relation between a back projection phase width and image noise in the conventional view weight.

As being apparent from FIG. 6, if the conventional view weight is used, it is found that noise characteristics are largely changed around a back projection phase width F of 1.0.

In general, the wider the back projection phase width is, the less the amount of noise of the reconstructed image becomes.

In order to avoid noise irregularities in the reconstructed image, it is assumed that the image is reconstructed using the same back projection phase width irrespective of the image position as Japanese Patent No. 4360817. Specifically, it is assumed that the narrowest back projection phase width that can be used in the image is used. In this case, if the back projection phase width in accordance with a case in which a large subject is imaged is always used, the number of pieces of projection data that are not used when a small subject is imaged is increased. Namely, although noise on the reconstructed image can be reduced, noise is increased. On the contrary, if the back projection phase width in accordance with a case in which a small subject is imaged is always used, temporal resolution is deteriorated and the artifact occurs due to a lack of available projection data when a large subject is imaged.

In the case where a whole body is imaged, an entire image is created with a large FOV, and then an image is created with a desired small FOV. In this case, it is desirable that if the reconstruction FOV is changed, the image quality (noise and temporal resolution) is not changed. Because when an image is reconstructed with a small FOV, the artifact that does not occur with a large FOV possibly occurs. In general, the back projection phase width is calculated on the basis of the settable maximum FOV. Because if the back projection phase width calculated with an FOV smaller than the maximum FOV is used, a data loss occurs when an image is reconstructed with a larger FOV.

In the case where the back projection phase width is determined with the reconstruction FOV, the projection data that can be used to generate an image within the reconstruction FOV can be maximally used. Thus, the back projection phase width becomes wider, and noise can be considerably reduced. On the contrary, an image with different noise and temporal resolution is created in accordance with the reconstruction FOV, and the stationarity of the image quality is deteriorated. In other words, in the case where an image is reconstructed with a wide reconstruction FOV and then is reconstructed while enlarging a local area with a narrow FOV, the image quality is changed.

In the case where the back projection phase width is narrowly set so as to enhance the temporal resolution, an image with less influence of the motion of the subject can be obtained, and an image with stable noise can be advantageously obtained irrespective of reconstructed slices. On the contrary, the ratio of unused projection data is increased to disadvantageously increase noise.

As compared to a case in which the subject is small, in the case where the subject is large, a loss of imaged data occurs when the bed moving speed is increased. In this case, if the projection data is extrapolated in the detector array direction to compensate the projection data, the artifact caused by extrapolation errors occurs in some cases.

In order to address these problems, Japanese Patent No. 4612347 proposes a method in which more projection data to be reconstructed can be used by calculating a weight normalized on the basis of the weight dependent on the cone angle to be used for the back projection. In this method, more projection data can be used, and thus an image with less noise can be obtained. Further, using the weight dependent on the cone angle, the extrapolation errors can be reduced. However, in the case where the method described in Japanese Patent No. 4612347 is used, the back projection phase width randomly differs in accordance with a position in the axial plane. The random difference of the back projection phase width causes random noise irregularities and temporal resolution irregularities in the reconstructed image. Further, noise irregularities in the axial plane appear in a striped shape (band shape) on the MPR.

For example, a head is diagnosed on the basis of a difference between the right brain and the left brain in some cases. Further, generation of noise irregularities between the right side and the left side in a bilaterally symmetric site such as a head or a breast is not desirable because the visibility of a lesion is deteriorated, possibly leading to a misdiagnosis. Further, in an image of the subject who moves, blurring or a motion artifact occurs due to temporal resolution irregularities. A significant difference between the right side and the left side in the reconstructed image of the subject caused by the blurring and the motion artifact is not desirable at the time of diagnosing.

In order to solve the above-described problems, the X-ray CT apparatus 1 in the embodiment executes an image reconstruction method in which a tomographic image without noise irregularities at the upper, lower, left, and right positions relative to the reference position on the axial image, without striped noise irregularities in the slice direction on the MPR image, without discontinuity of the image quality, and with less noise by enhancing the data use efficiency can be generated using an easier process.

Next, an image reconstruction method in the embodiment will be described with reference to FIG. 7 to FIG. 19.

Figure 7:
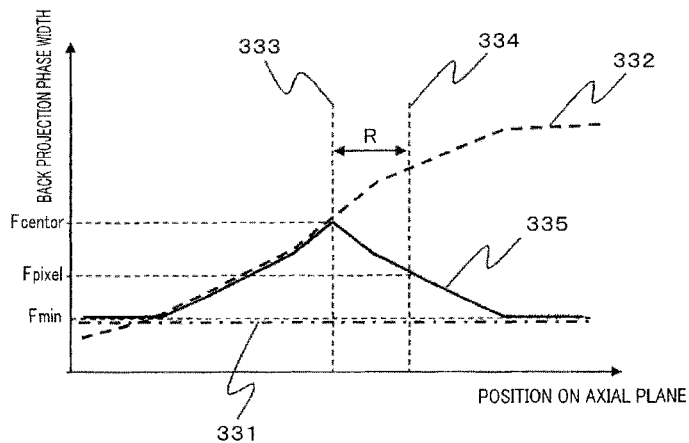
FIG. 7 is a diagram for explaining a difference between the conventional technique and the present invention related to the back projection phase width on an axial plane.

FIG. 7 shows a difference of the back projection phase width on the axial plane between the conventional technique and the embodiment. The horizontal axis represents a position on a line connecting a position that is located on the axial plane and where the back projection phase width becomes smallest on the axial plane to the reference position. The vertical axis represents the back projection phase width.

As the image reconstruction methods in the conventional technique, there are two methods: one method as describe in Japanese Patent No. 4360817 (conventional method 1) in which the back projection phase width is set at a certain value and the smallest value that can be used in the image is used; and the other method as described in Japanese Patent No. 4612347 (conventional method 2) in which the back projection phase width is set at a variable value for each pixel and the value with which the projection data can be used most in each pixel is used.

FIG. 7 shows an example of a graph in which 331 denotes the back projection phase width on the basis of the conventional method 1, and 332 denotes the back projection phase width on the basis of the conventional method 2. In the conventional method 1, noise irregularities are small because the certain back projection phase width is used irrespective of a position. However, noise is increased because the back projection phase width becomes narrower. In the conventional method 2, a wide back projection phase width can be used in accordance with a position. However, the back projection phase width, namely, the amount of noise differs depending on a position, and the relation of the levels of noise becomes a revolution shape around the rotational center axis in accordance with a slice. Specifically, when creating the MPR, striped noise irregularities are generated.

On the other hand, the reference position is set on the axial image in the image reconstruction method of the embodiment. In the example of FIG. 7, a reference position 333 is one reference point and an scanning center position.

Further, in the image reconstruction method of the embodiment, the back projection phase width in each pixel is calculated in accordance with a function of a distance R from the reference position 333 to a reconstruction pixel position 334.

FIG. 7 shows an example of a graph in which 335 denotes the back projection phase width in the embodiment. 335 is calculated in accordance with a function of the distance R from the reference position 333 to the reconstruction pixel position 334. The shape of the function to determine 335 is bilaterally symmetrical at the reference position 333, and is monotonically decreased in accordance with the distance R from the reference position. Namely, in the image reconstruction method of the embodiment, the back projection phase width in each pixel is calculated so as to have the same value in a concentric manner from the reference position 333 in the axial plane in accordance with a predetermined function.

According to the image reconstruction method in the embodiment, the amount of data used is the same even if the slice is changed as long as the position on the axial plane is the same. Thus, even if the slice position is changed, striped noise irregularities are not generated when the MPR is created as in the conventional method 2.

According to the image reconstruction method in the embodiment, the back projection phase width and the view weighting function shape are continuously changed in accordance with the distance from one or more reference points on the axial plane. Thus, changes of noise caused by changes of the back projection phase width in accordance with the slice position can be eliminated. Further, an image with less noise can be generated by efficiently using the projection data while maintaining continuous changes of noise in the axial plane.

<Method in the case where the reference position is one reference point and the reference point is located at the rotational center position>

Figure 8:
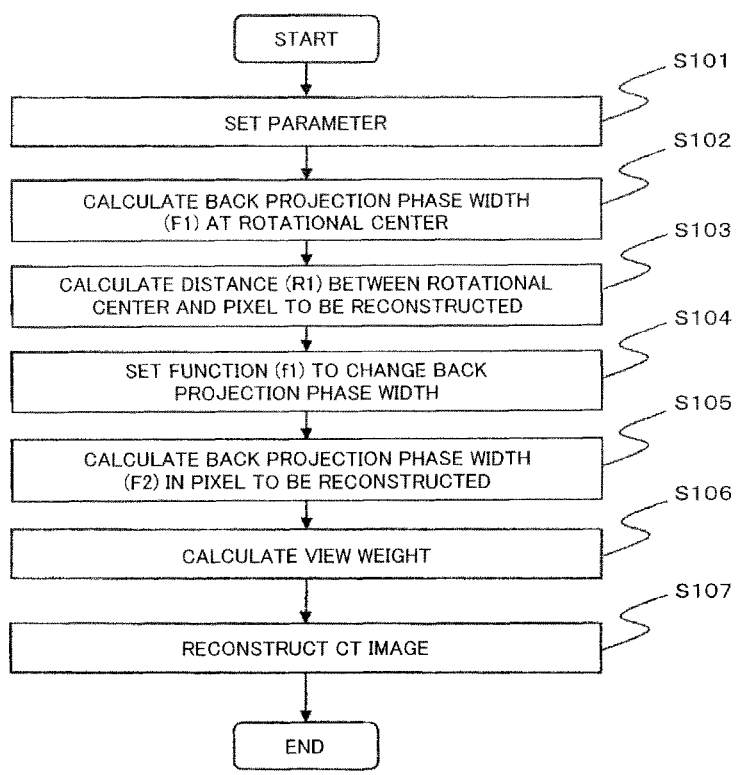
FIG. 8 is a flowchart for showing a processing flow of the X-ray CT apparatus in the case where a reference position is one reference point and the reference point is located at a rotational center position.

As shown in FIG. 8, the central control device 200 of the X-ray CT apparatus 1 accepts setting of parameters to perform scanning (S101). The central control device 200 displays a parameter setting screen illustrated in FIG. 9 on the display device 211, and accepts setting of the parameters through the input device 212.

Figure 9:
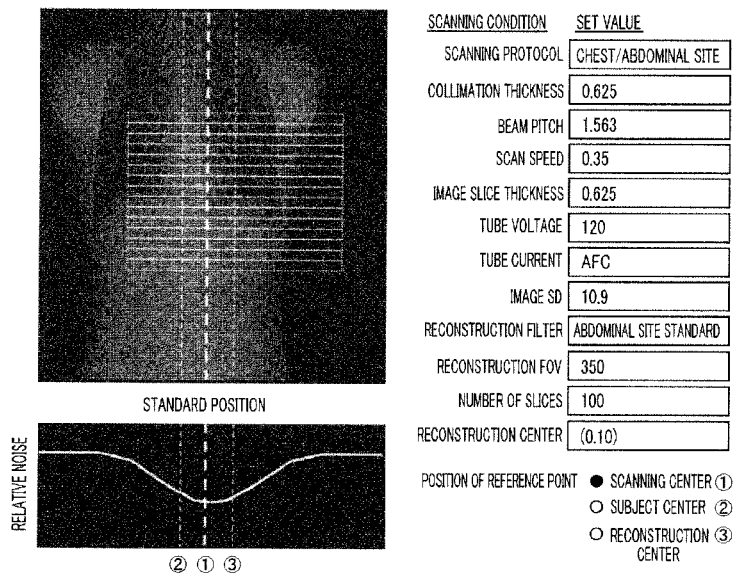
FIG. 9 shows an example of a parameter setting screen.

As shown in FIG. 9, the parameters set in S101 include an scanning protocol, a collimation thickness, a beam pitch, a scan speed, an image slice thickness, tube voltage, tube current, an image SD, a reconstruction filter, a reconstruction FOV, the number of slices, a reconstruction center, the position of the reference point, and the like.

For example, the scanning protocol is set for a scanogram image for positioning shown in FIG. 9, a recommended value related to the position of the reference point is initialized together with the scanning conditions and the reconstruction conditions such as the collimation thickness, the beam pitch, the image slice thickness, the reconstruction filter, the reconstruction center, and the reconstruction FOV.

In this case, the position of the reconstruction center is initialized at the rotational center on the scanogram. The reconstruction FOV is initialized at an FOV in accordance with a site. These can be arbitrarily changed if needed. Further, the position of the reference point is usually initialized at the rotational center. The position of the reference point can be changed to any one of the subject center, the reconstruction center, and arbitrary one or more positions if needed. In the setting example of the reference point shown in FIG. 9, the position of the reference point is set at the subject center. In this setting example, even in the case where the subject does not exist at the rotational center position, noise characteristics symmetrical at the upper, lower, left, and right positions from the subject center can be realized. Further, the position of the reference point is set at the reconstruction center, so that noise characteristics symmetrical at the upper, lower, left, and right positions from the subject center can be realized even in the case where the subject does not exist at the rotational center position and one arm is located in the scanning field of view.

Further, before or after the scanning, the central control device 200 of the X-ray CT apparatus 1 sets values of parameters such as a bed moving speed T, the number of detector arrays Nv, the number of extrapolation arrays, a slope width γ, a back projection phase width lower limit $F_{min}$, and a slope width lower limit $γ_{min}$ on the basis of the values of the parameters input by the user or by reading the values stored in the storage device 213.

It is desirable that the lower limit $γ_{min}$ of the slope width satisfies $γ_{min}≧0$, and the lower limit $F_{min}$ of the back projection phase width satisfies $F_{min}÷0.5+γ_{min}$. Accordingly, the minimum number of views required for image reconstruction can be secured while maintaining the slope width of the view weight necessary to correct the motion artifact and the helical artifact.

In this case, the parameter of the reference position will be described. The reference position is defined by, at least, one or more reference points. Further, as will be described later, the reference position may be defined by a combination of one or more reference points and the reference plane.

In the case where the reference position is defined by one reference point, the position of the reference point is the scanning center position, the subject center position, the reconstruction center position, or the like as illustrated in FIG. 9. In the example of FIG. 9, the scanning center position is set as the position of the reference point.

FIG. 9 illustrates a graph of relative noise to a position on the axial plane under the scanogram obtained by the scanning for positioning. In the graph of relative noise, the horizontal axis denotes a position on the axial plane and the vertical axis denotes relative noise. In the example of FIG. 9, the position of the reference point is set at the scanning center position, and thus the relative noise is bilaterally symmetrical relative to the scanning center positron. It should be noted that the "scanning center" and the "rotational center" are synonymous in the embodiment, and thus are hereinafter unified to the term of the "rotational center".

As shown in FIG. 9, the graph of the relative noise to the position on the axial plane is displayed on the parameter setting screen, so that generation of an axial image without noise irregularities on the left and right sides relative to the reference position can be visualized. Further, the reference position is displayed while being overlapped with the scanogram, so that the user can easily adjust the noise characteristics of the CT image in accordance with a diagnostic area.

Figure 10:
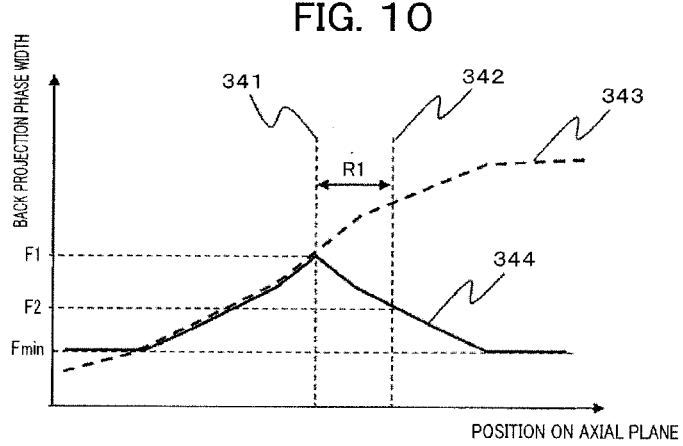
FIG. 10 is an explanatory diagram of a method in the case where the reference position is one reference point and the reference point is located at the rotational center position.

Next, the computation device 202 of the X-ray CT apparatus 1 inputs the parameters set in S101, and calculates a back projection phase width (F1) at the rotational center (S102). FIG. 10 illustrates a rotational center position 341 and the back projection phase width F1 relative to the rotational center position.

Next, the computation device 202 calculates a distance (R1) between the rotational center position as the reference position and the pixel to be reconstructed (S103). FIG. 10 illustrates a pixel position 342 to be reconstructed and the distance R1 between the rotational center position and the pixel to be reconstructed.

Next, the computation device 202 sets a function (f1) to change the back projection phase width in accordance with the distance (R1) between the rotational center position as the reference position and the pixel to be reconstructed (S104). FIG. 10 illustrates a graph 349 for showing the function (f1) to change the back projection phase width. The graph 344 shows an orbit of the function (f1) to change the back projection phase width that is turned back at the reference position (rotational center position 341). It should be noted that FIG. 10 illustrates a graph 343 of the back projection phase width with which the projection data can be used most in each pixel for reference.

Next, the computation device 202 assigns the value of the distance (R1) between the rotational center position as the reference position and the pixel to be reconstructed to the function (f1) to change the back projection phase width, so that a back projection phase width (F2) in the pixel to be reconstructed is calculated (S105). Specifically, the computation device 202 calculates F2=f1(R1). FIG. 10 illustrates the back projection phase width F2 relative to the pixel position to be reconstructed. It should be noted that FIG. 10 illustrates the narrowest back projection phase width lower limit $F_{min}$ that can be used in an image for reference.

Next, the computation device 202 corrects the back projection phase width F2 in the pixel to be reconstructed and the slope width γ of the view weighting function, so that F2 is larger than $F_{min}$ and the slope width γ of the view weighting function is larger than the lower limit $γ_{min}$ of the slope width but smaller than the back projection phase width F2−0.5 in each pixel. Then, the computation device 202 calculates the view weight on the basis of the corrected back projection phase width F2 in the pixel to be reconstructed and the corrected slope width γ of the view weighting function (S106).

Next, the computation device 202 reconstructs the CT image using the view weight calculated in S106 (S107). The reconstruction process of the CT image using the view weight uses, for example, the following equation.

$$I(x, y, z) = \frac{1}{\pi} \int_{\phi_1(x,y,z)}^{\phi_2(x,y,z)} \int_{-\infty}^{\infty} W_p(\phi, R) \cdot P_p(\phi, t', v) \cdot g(t - t') \cdot dt' \cdot d\phi \quad (5)$$

wherein I represents image data; x, y, and z, a position (mm) of a pixel to be reconstructed; $F_{pixel}(x, y)$, the back projection phase width of the pixel to be reconstructed; $W_p(\cdot)$, a view weight for the parallel beam; Ø, a projection angle (rad) of the parallel beam; $P_p(\cdot)$, projection data; t, a parallel beam channel position (mm); υ, a detector array position (mm); and $g(\cdot)$, a reconstruction filter.

As described above, the computation device 202 calculates the back projection phase width in each pixel so as to have the same value in a concentric manner from the reference position as the rotational center position in the axial plane. Thus, it is possible to realize noise characteristics that are symmetrical at the upper, lower, left, and right positions relative to the subject placed at the rotational center position.

Further, as a modified example, the computation device 202 may calculate the back projection phase width in each pixel so as to be monotonically narrowed relative to the distance from the reference position as the subject center position in the axial plane and so as to have the same value in a concentric manner as illustrated in FIG. 9. Accordingly, even in the case where the subject is placed while being shifted from the rotational center, the back projection phase width (the amount of noise) that is symmetrical at the upper, lower, left, and right positions relative to the subject can be realized.

Further, as another modified example, the computation device 202 may calculate the back projection phase width in each pixel so as to be monotonically narrowed relative to the distance from the reference position as the reconstruction center position in the axial plane and so as to have the same value in a concentric manner as illustrated in FIG. 9. Accordingly, while the deterioration of the image quality caused by data extrapolation in the detector array direction at the position apart from the revolution center is suppressed, noise can be reduced by using more projection data at the revolution center position.

Further, as still another modified example, the computation device 202 may calculate the back projection phase width in each pixel on the basis of the reduction rate of the back projection phase width relative to the reference position at the position apart from the reference position only by the reference distance. Accordingly, the back projection phase width at an arbitrary position in the axial image can be easily determined.

<First method in the case where the reference position is one reference point and the reference point is located at a position apart from the rotational center>

Figure 11:
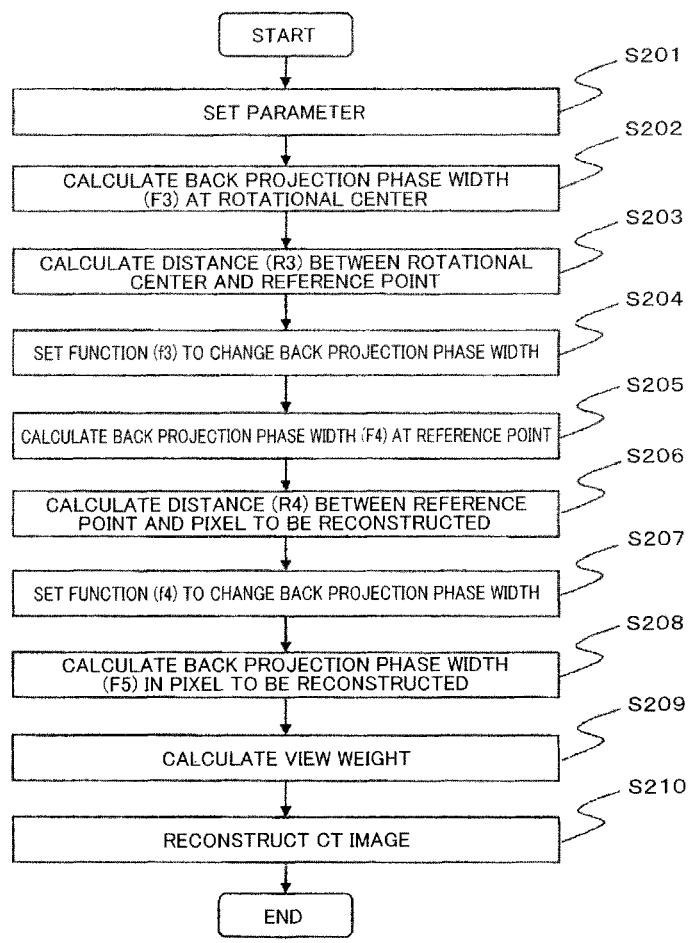
FIG. 11 is a flowchart for showing a processing flow of the X-ray CT apparatus in the case where the reference position is one reference point and the reference point is located at a position apart from the rotational center.

As shown in FIG. 11, the central control device 200 of the X-ray CT apparatus 1 accepts setting of parameters to perform scanning (S201). The central control device 200 displays the parameter setting screen illustrated in FIG. 9 on the display device 211, and accepts setting of the parameters through the input device 212.

Further, before or after the scanning, the central control device 200 of the X-ray CT apparatus 1 sets values of parameters such as a bed moving speed T, the number of detector arrays Nv, the number of extrapolation arrays, a slope width γ, a back projection phase width lower limit $F_{min}$, and a slope width lower limit $γ_{min}$ on the basis of the values of the parameters input by the user or by reading the values stored in the storage device 213.

Figure 12:
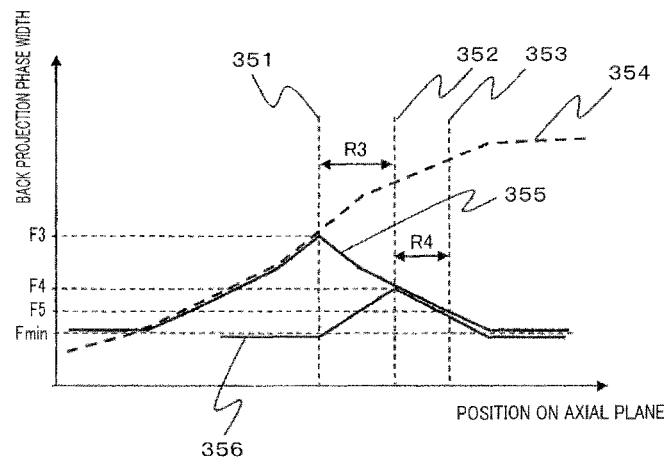
FIG. 12 is an explanatory diagram of a first method in the case where the reference position is one reference point and the reference point is located at the position apart from the rotational center.

FIG. 12 shows a rotational center position 351 and a position 352 apart from the rotational center position. In the process shown in the flowchart of FIG. 11, the reference point is the position 352 apart from the rotational center position.

Next, the computation device 202 of the X-ray CT apparatus 1 inputs the parameters set in S201, and calculates a back projection phase width (F3) at the rotational center (S202). FIG. 12 illustrates the back projection phase width F3 relative to the rotational center position 351.

Next, the computation device 202 calculates a distance (R3) between the rotational center position and the reference point (S203). FIG. 12 illustrates the distance R3 between the rotational center position 351 and the reference point (position apart from the rotational center) 352.

Next, the computation device 202 sets a function (f3) to change the back projection phase width in accordance with the distance (R3) between the rotational center position and the reference point (S204). FIG. 12 illustrates a graph 355 for showing the function (f3) to change the back projection phase width. The graph 355 shows an orbit of the function (f3) to change the back projection phase width that is turned back at the rotational center position 351. It should be noted that FIG. 12 illustrates a graph 354 of the back projection phase width with which the projection data can be used most in each pixel for reference.

Next, the computation device 202 assigns the value of the distance (R3) between the rotational center position and the reference point to the function (f3) to change the back projection phase width, so that a back projection phase width (F4) at the reference point is calculated (S205). Specifically, the computation device 202 calculates F4=f3(R3). FIG. 12 illustrates the back projection phase width F4 at the reference point (position apart from the rotational center) 352.

Next, the computation device 202 calculates a distance (R4) between the reference point and the pixel to be reconstructed (S206). FIG. 12 illustrates the distance R4 between the reference point (position apart from the rotational center) 352 and a pixel position 353 to be reconstructed.

Next, the computation device 202 sets a function (f4) to change the back projection phase width in accordance with the distance (R4) between the reference point and the pixel to be reconstructed (S207). FIG. 12 illustrates a graph 356 for showing the function (f4) to change the back projection phase width. The graph 356 shows an orbit of the function (f4) to change the back projection phase width that is turned back at the reference point (position apart from the rotational center) 352.

Next, the computation device 202 assigns the value of the distance (R4) between the reference point and the pixel to be reconstructed to the function (f4) to change the back projection phase width, so that a back projection phase width (F5) in the pixel to be reconstructed is calculated (S208) Specifically, the computation device 202 calculates F5=f4(R4). FIG. 12 illustrates the back projection phase width F5 in the pixel position 353 to be reconstructed. It should be noted that FIG. 12 illustrates the narrowest back projection phase width lower limit $F_{min}$ that can be used in an image for reference.

Next, the computation device 202 corrects the back projection phase width F5 in the pixel to be reconstructed and the slope width γ of the view weighting function, so that F5 is larger than $F_{min}$ and the slope width γ of the view weighting function is larger than the lower limit $γ_{min}$ of the slope width but smaller than the back projection phase width F5−0.5 in each pixel. Then, the computation device 202 calculates the view weight on the basis of the corrected back projection phase width F5 in the pixel to be reconstructed and the corrected slope width γ of the view weighting function (S209).

Next, the computation device 202 reconstructs the CT image using the view weight calculated in S209 (S210). The reconstruction process of the CT image using the view weight is the same as S107.

<Second method in the case where the reference position is one reference point and the reference point is located at a position apart from the rotational center>

The processing flow in the second method is the same as that in the first method described with reference to FIG. 11 and FIG. 12, and thus the illustration is omitted.

The second method is different from the first method in the shape of the function to change the back projection phase width. In the first method, the back projection phase width at the reference point is determined using the function that is bilaterally symmetrical to the rotational center. However, the second method uses the back projection phase width larger than that of the first method that is smaller than the maximum back projection phase width at the reference point as shown in FIG. 13.

Figure 13:
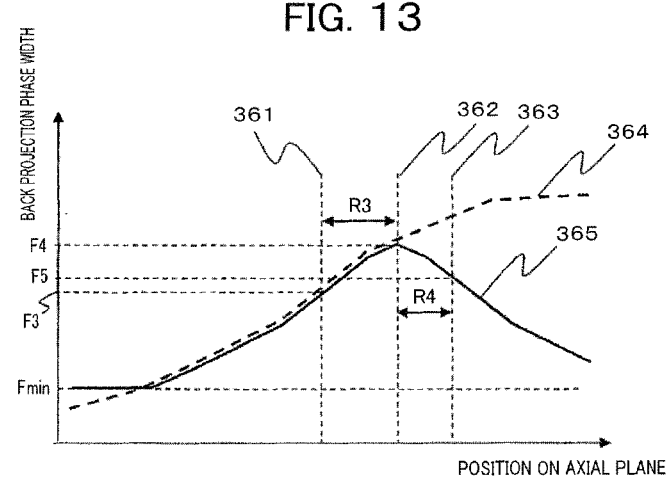
FIG. 13 is an explanatory diagram of a second method in the case where the reference position is one reference point and the reference point is located at the position apart from the rotational center.

FIG. 13 illustrates the back projection phase width F3 relative to a rotational center position 361. Further, the distance R3 between the rotational center position 361 and a reference point 362 is illustrated. Further, a graph 365 for showing a function (f3) to change the back projection phase width is illustrated. The graph 365 shows an orbit of the function (f3) to change the back projection phase width that is turned back at the reference point 362. It should be noted that FIG. 13 illustrates a graph 364 of the back projection phase width with which the projection data can be used most in each pixel for reference. Further, the back projection phase width F4 at the reference point 362 is illustrated. Further, the distance R4 between the reference point 362 and a pixel position 363 to be reconstructed is illustrated.

In FIG. 12, the back projection phase width F4 at the reference point (position pa from the rotational center) 352 is a value smaller than the maximum back projection phase width. In FIG. 13, the back projection phase width F4 at the reference point 362 is the same value as the maximum back projection phase width.

In the case of using the second method, striped noise irregularities are likely to be generated in the MPR image as compared to the case of using the first method. However, an axial image symmetrical to the reference point and with noise reduced can be obtained.

<Method in the case where the reference positions are two reference points>

Figure 14:
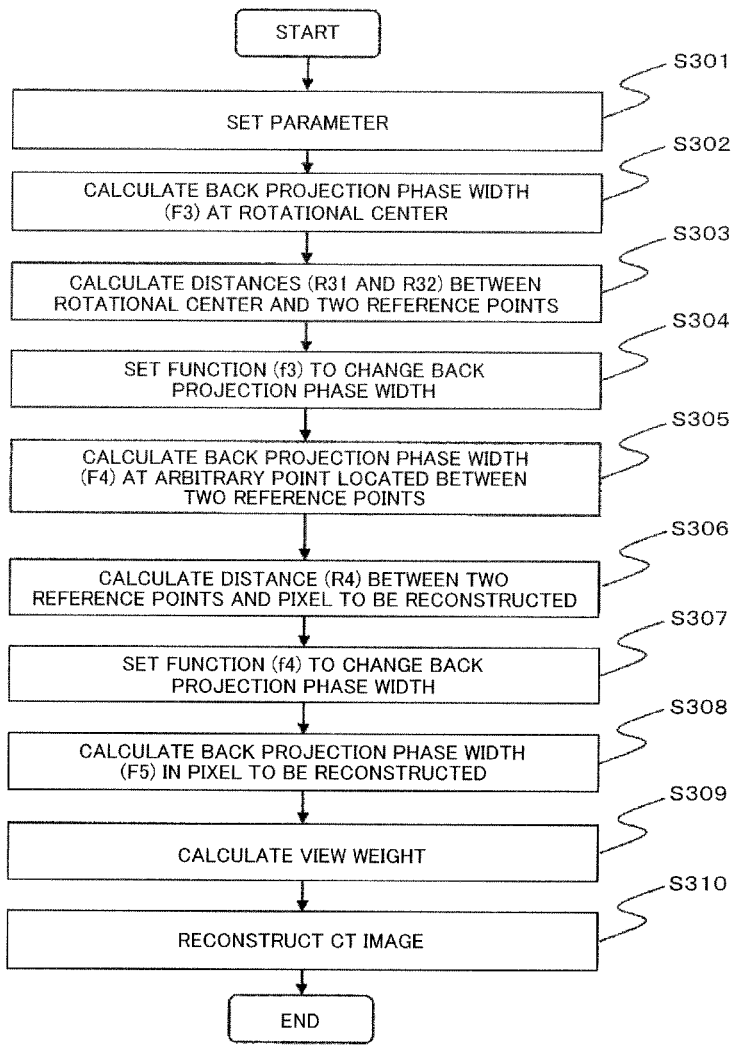
FIG. 14 is a flowchart for showing a processing flow of the X-ray CT apparatus in the case where the reference positions are two reference points.

As shown in FIG. 14, the central control device 200 of the X-ray CT apparatus 1 accepts setting of parameters to perform scanning (S301). The central control device 200 displays the parameter setting screen illustrated in FIG. 9 on the display device 211, and accepts setting of the parameters through the input device 212.

Further, before or after the scanning, the central control device 200 of the X-ray CT apparatus 1 sets values of parameters such as a bed moving speed T, the number of detector arrays Nv, the number of extrapolation arrays, a slope width γ, a back projection phase width lower limit $F_{min}$, and a slope width lower limit $γ_{min}$ on the basis of the values of the parameters input by the user or by read the values stored in the storage device 213.

Figure 15:
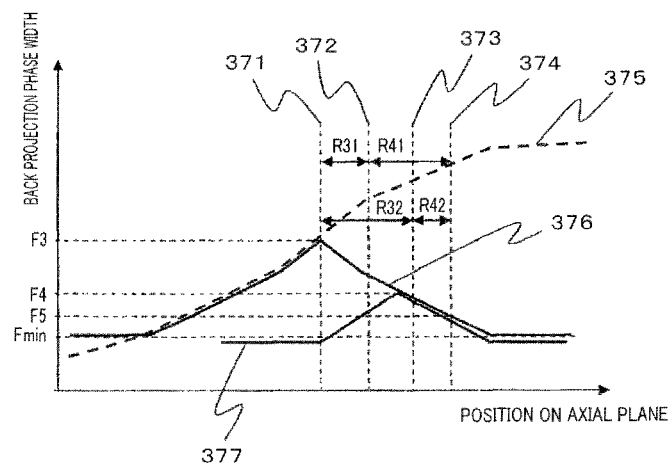
FIG. 15 is an explanatory diagram of a calculation process of the back projection phase width in the case where the reference positions are two reference points.

FIG. 15 shows a rotational center position 371 and positions 372 and 373 apart from the rotational center position. In the process shown in the flowchart of FIG. 15, the two reference points are the positions 372 and 373 apart from the rotational center position.

Next, the computation device 202 of the X-ray CT apparatus 1 inputs the parameters set in S301, and calculates the back projection phase width (F3) at the rotational center (S302). FIG. 15 illustrates the back projection phase width F3 relative to the rotational center position 371.

Next, the computation device 202 calculates distances (R31 and R32) between the rotational center position and the two reference points (S303). FIG. 15 illustrates the distances R31 and R32 between the rotational center position 371 and the two reference points 372 and 373.

Next, the computation device 202 sets the function (f3) to change the back projection phase width in accordance with the distances (R31 and R32) between the rotational center position and the two reference points (S304). FIG. 15 illustrates a graph 376 for showing the function (f3) to change the back projection phase width. The graph 376 shows an orbit of the function (f3) to change the back projection phase width that is turned back at the rotational center position 371. It should be noted that FIG. 15 illustrates a graph 375 of the back projection phase width with which the projection data can be used most in each pixel for reference.

Next, the computation device 202 assigns the values of the distances (R31 and R32) between the rotational center position and the two reference points to the function (f3) to change the back projection phase width, so that the back projection phase width (F4) at an arbitrary point located between the two reference points is calculated (S305). Specifically, the computation device 202 calculates F4=f3(R31 and R32). FIG. 15 illustrates the back projection phase width F4 at the arbitrary point located between the two reference points.

Next, the computation device 202 calculates the distance (R4) between the two reference points and the pixel to be reconstructed (S306). FIG. 15 illustrates the distances R41 and R42 between the two reference points 372 and 373 and a pixel position 374 to be reconstructed.

Next, the computation device 202 sets the function (f4) to change the back projection phase width in accordance with the distances (R41 and R42) between the two reference points and the pixel to be reconstructed (S307). FIG. 15 illustrates a graph 377 for showing the function (f4) to change the back projection phase width. The graph 377 shows an orbit of the function (f3) to change the back projection phase width that is turned back at the arbitrary point located between the two reference points.

Next, the computation device 202 assigns the values of the distances (R41 and R42) between the two reference points and the pixel to be reconstructed to the function (f4) to change the back projection phase width, so that the back projection phase width (F5) in the pixel to be reconstructed is calculated (S308). Specifically, the computation device 202 calculates F5=f4(R41 and R42). FIG. 15 illustrates the back projection phase width F5 in the pixel position 374 to be reconstructed. It should be noted that FIG. 15 illustrates the narrowest back projection phase width lower limit $F_{min}$ that can in an image for reference.

Next, the computation device 202 corrects the back projection phase width F5 in the pixel to be reconstructed and the slope width γ of the view weighting function, so that F5 is larger than $F_{min}$ and the slope width γ of the view weighting function is larger than the lower limit $γ_{min}$ of the slope width but smaller than the back projection phase width F5−0.5 in each pixel. Then, the computation device 202 calculates the view weight on the basis of the corrected back projection phase width F5 in the pixel to be reconstructed and the corrected slope width γ of the view weighting function (S309).

Next, the computation device 202 reconstructs the CT image using the view weight calculated in S309 (S310). The reconstruction process of the CT image using the view weight is the same as S107.

<Method in the case where the reference position is a combination of a reference point and a reference plane>

In the multi-slice CT, the X-ray 108 spread in the slice direction is irradiated. Thus, in the case where 360-degree scanning is performed by normal scanning, the X-ray 108 is continued to be irradiated 360 degrees in each pixel of the center slice. On the contrary, there is a phase in which no X-ray 108 is irradiated at a position apart from the center slice. This is because for a pixel that is shorter in distance from the X-ray generation device 102 (X-ray source), the cone angle of the projection data used becomes larger. Therefore, as shown in FIG. 16, it is desirable that the reference plane is set at the center slice, and the back projection phase width is narrowed in accordance with a distance from the center slice. Accordingly, the influence of the interpolation process in the detector array direction can be suppressed at the time of the normal scanning, and errors caused by interpolation can be reduced.

Figures 16A, 16B:
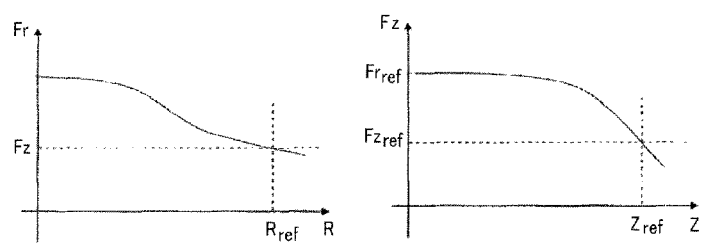
FIG. 16 are explanatory diagrams of a calculation process of the back projection phase width in the case where the reference position is a combination of the reference point and a reference plane.

FIG. 16A shows a graph of a back projection phase width $F_r$ (vertical axis) relative to a distance R (horizontal axis) between the reference point on the reference plane and the pixel to be reconstructed. FIG. 16B shows a graph of a back projection phase width $F_z$ (vertical axis) relative to a distance Z (horizontal axis) from the reference plane to the pixel to be reconstructed.

In the graphs, $R_{ref}$ represents a reference distance; Fz, a back projection phase width relative to a distance (Z) in the z-direction from the reference plane to the pixel to be reconstructed at the position of the reference distance ($R_{ref}$; $Z_{ref}$, a reference distance in the z-direction; $Fz_{ref}$, a back projection phase width at the reference distance ($Z_{ref}$) in the z-direction; and $Fr_{ref}$, a back projection phase width at the reference position ($R_{ref}$) when Z=0.

As described above, in the case where the projection data can be obtained by the axial scanning, the computation device 202 may narrow the back projection phase width in each pixel in accordance with a distance from the reference slice in the body axis direction. Accordingly, the influence of interpolation in the detector array direction in a slice apart from the center slice can be reduced without deteriorating the data efficiency at the center slice.

<Example of calculation equation of distance>

Each of the followings shows an example of a calculation equation of a distance from the reference position on the axial plane to the pixel to be reconstructed.

$$R = \sqrt{(x-x_{r1})^2 + (y-y_{r1})^2} \quad (6)$$

$$R = \sqrt{\frac{(x-x_{r1})^2 + (y-y_{r1})^2 + (x-x_{r2})^2 + (y-y_{r2})^2}{2}} \quad (7)$$

$$R = \sqrt{\frac{\sum_{n=1}^{N}(x-x_{rn})^2 + (y-y_{rn})^2}{N}} \quad (8)$$

wherein $x_{rn}$ and $y_{rn}$ (n are indexes 1 to N of N reference points) represent reference positions, and R represents a distance from the reference position to the pixel to be reconstructed.

In the case where the reference point is one point, the computation device 202 sets the distance between the pixel position to be reconstructed and the reference point as R. Further, in the case where the reference points are 2 or more points, the computation device 202 calculates R on the basis of a combined vector defined using plural reference points.

The following is an example of a calculation equation of a distance from the reference plane to the pixel to be reconstructed.

$$Z = \sqrt{(z-z_r)^2} \quad (9)$$

wherein $z_r$ represents a position on the reference plane in the detector array direction, and Z represents a distance from the reference plane to the pixel to be reconstructed.

<Example of function to change back projection phase width>

The following is an example of a linear function to change a back projection phase width.

$$f_F(X, X_{ref}) = F + (F_{ref} - F) \cdot \frac{X}{X_{ref}} \quad (10)$$

wherein $f_F(\cdot)$ represents a linear function; X, a distance from the reference position to the pixel to be reconstructed or a distance from the reference plane to the pixel to be reconstructed; F, a back projection phase width at the reference position; $X_{ref}$, a reference distance; and $F_{ref}$, a back projection phase width at the reference distance.

Figure 17:
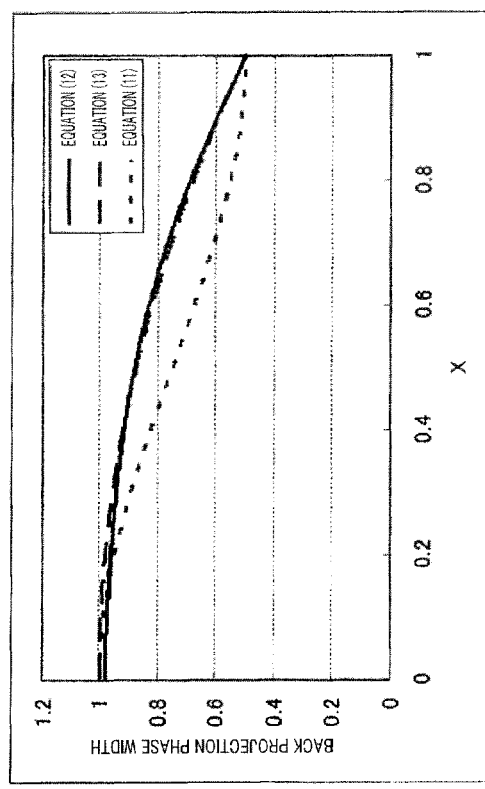
FIG. 17 shows an example of a non-linear function to change the back projection phase width.

The followings are four examples of non-linear functions to change a back projection phase width. In the embodiment, any one of the non-linear functions may be used, or a non-linear function other than the above may be used. It should be noted that the shapes of the following three functions are shown in FIG. 17.

Cubic Function $$f_F(X, X_{ref}) = F + (F_{ref} - F) \cdot \left(3 \cdot \left(\frac{X}{X_{ref}}\right)^2 - 2 \cdot \left(\frac{X}{X_{ref}}\right)^3\right) \quad (11)$$

Hyperbolic Tangent Function $$f_F(X, X_{ref}) = F + (F_{ref} - F) \cdot \left(1 - \tanh\left(k_z - \frac{k_z \cdot X}{X_{ref}}\right)\right) \quad (12)$$

Exponential Function $$f_F(X, X_{ref}) = F + (F_{ref} - F) \cdot \left(\frac{X}{X_{ref}}\right)^{k_z} \quad (13)$$

Quartic Function $$f_F(X, X_{ref}) = \quad (14)$$
$$F + (F_{ref} - F) \cdot \left\{a\left(\frac{X}{X_{ref}}\right)^4 + b\left(\frac{X}{X_{ref}}\right)^3 + c\left(\frac{X}{X_{ref}}\right)^2 + d\left(\frac{X}{X_{ref}}\right) + e\right\}$$

wherein $f_F(\cdot)$ represents a linear function; X, a distance from the reference position to the pixel to be reconstructed or a distance from the reference plane to the pixel to be reconstructed; F, a back projection phase width at the reference position; $X_{ref}$, a reference distance; $F_{ref}$, a back projection phase width at the reference distance; and $k_z$, a positive real number.

Using the above-described functions to change the back projection phase width in accordance with the distance from the reference point to the target pixel or the distance from the reference plane to the target pixel, the back projection phase width symmetrical relative to the reference point or the reference plane can be continuously changed. It should be noted that as shown in FIG. 16, both of the distance from the reference plane and the distance from the reference position can be used. The back projection phase widths $f_{RZ}$ (R, $R_{ref}$, Z, and $Z_{ref}$) in this case can be calculated in accordance with, for example, the following equations.

$$f_Z(Z, Z_{ref}) = Fr_{ref} + (Fz_{ref} - Fr_{ref}) \cdot \frac{Z}{Z_{ref}} \quad (15)$$

$$f_{RZ}(R, R_{ref}, Z, Z_{ref}) = F + (f_Z(Z, Z_{ref}) - F) \cdot \frac{R}{R_{ref}} \quad (16)$$

wherein $f_z(\cdot)$ represents a function (for axial scanning) to change a back projection phase width in accordance with Z; Z, a distance from the reference plane to the target pixel; $Z_{ref}$, a reference distance in the z-direction; $Fz_{ref}$, a back projection phase width at the reference distance ($Z_{ref}$) in the z-direction; $Fr_{ref}$, a back projection phase width at the reference position ($R_{ref}$) when Z=0; R, a distance from the reference position to the target pixel; $R_{ref}$, a reference distance; and F, a back projection phase width at the reference position.

<Example of method of determining reference position>

The methods of determining the reference position mainly include the following three methods.
(1) The reference position is set at the rotational center position.
(2) The reference position is set at the subject center position.
(3) The reference position is set at the reconstruction center position.

(1) The reference position is set at the rotational center position, and the above-described image reconstruction method is executed, so that the noise characteristics become symmetrical relative to the rotational center position. Further, data can be most efficiently used for the subject placed at the rotational center position. Further, the image reconstruction method is effective because the subject is placed at the rotational center position in many cases and the site to be diagnosed is located near the rotational center position. The rotational center position can be easily determined without using the projection data.

(2) The reference position is et at the subject center position, and the above-described image reconstruction method is executed, so that the noise characteristics become symmetrical relative to the subject center position even in the case where the subject is placed while being shifted from the rotational center position. The image reconstruction method is effective even when right and left lung fields are compared to each other. The subject center position can be determined by calculating the position of the center of gravity of the subject in the projection data.

(3) The reference position is set at the reconstruction center position, and the above-described image reconstruction method is executed, so that the noise characteristics become symmetrical relative to the reconstruction center position. The image reconstruction method is effective when the reconstruction center corresponds to the site to be diagnosed. The reconstruction center position can be determined using a value input through the input device 212 on the parameter setting screen illustrated in FIG. 9.

In this case, the values of the base variables to calculate the back projection phase width at the reference position and the reference point, the back projection phase width at the reference distance, and the back projection phase width in each pixel such as the lower limit of the back projection phase width, the view weight slope width, and the lower limit of the slope width may be fixed irrespective of a site, and may be changed in accordance with a site, an scanning protocol, and a reconstruction filter. The computation device 202 changes the values of the base variables in accordance with a site, so that desired image quality in accordance with a site can be realized. Further, the computation device 202 changes the values of the base variables in accordance with a reconstruction filter, so that a desired back projection phase width in accordance with a site can be easily set.

For example, in the case of a site such as a lung field or a head in which the left and right sides are compared to each other, the reference point is desirably set at the subject center position. On the other hand, in the case of a site such as an abdominal site in which noise is likely to increase, the reference point is desirably set at the rotational center position so that the noise can be reduced most. In the case of a site such as a lower limb, two reference points are desirably set at a left leg and a right leg, or the reference point is desirably set at the subject center position.

Further, in the case of a site such as a lower abdominal site that largely moves, the slope width of the view weight and the lower limit of the slope width are desirably set at a wide range to reduce the motion artifact. On the other hand, in the case of a site such as a head that moves less, the slope width of the view weight and the lower limit of the slope width are desirably set at a narrow range to reduce noise.

<Example of calculation equation of back projection phase width>

The following is an example of a calculation equation of a back projection phase width in the case where the reference point is the rotational center position. This corresponds to the phase width with which the X-ray 108 is irradiated at the rotational center position when being imaged at the bed moving speed T.

$$F = \frac{\Delta v \cdot (N_v + N_v' - 1) \cdot D}{W \cdot T} \quad (17)$$

wherein F represents a back projection phase width; $\Delta v$, the size of elements in the detector array direction; $N_v$, the number of detector arrays; $N_v'$, the number of detector extrapolation arrays; D, a distance between the X-ray generation device 102 (X-ray source) and the rotational center position; W, a distance between the X-ray generation device 102 (X-ray source) and the X-ray detection device 103; and T, a bed moving speed.

<Restriction equation of parameter>

The followings are the upper limit and the lower limit of the back projection phase width, and the upper limit and the lower limit of the slope width of the view weighting function. Basically, a set value is used for the slope width of the view weight.

However, in the case where the back projection phase width becomes narrow and the set slope width cannot be secured, values limited by the following lower limits are used.

$$\gamma_{min} = F_{min} - 0.5(\gamma_{min} F_{min} - 0.5) \quad (18)$$

$$F = F_{min}(F < F_{min}) \quad (19)$$

$$\gamma = F - 0.5(\gamma < F - 0.5) \quad (20)$$

$$\gamma = \gamma_{min}(\gamma < \gamma_{min}) \quad (21)$$

wherein $\gamma$ represents the slope width of the view weight; F, a back projection phase width; $\gamma_{min}$, the lower limit of the view weight slope width; and $F_{min}$, the lower limit of the back projection phase width.

Further, in the case where a non-linear function is used in the calculation process of the back projection phase width, values limited by the following upper limits are used when the back projection phase width becomes excessively large.

$$F = F_{max}(F > F_{max}) \quad (22)$$

$$\gamma = \gamma_{max}(\gamma > \gamma_{max}) \quad (23)$$

wherein $\gamma$ represents the slope width of the view weight; F, a back projection phase width; $\gamma_{max}$, the upper limit of the view weight slope width; and $F_{max}$, the upper limit of the back projection phase width.

Even in the case where the back projection phase width is changed using the back projection phase width index $F_{ref}$ at the distance R from the reference position and the reference distance $R_{ref}$ by the above-described restriction equations, it is possible to prevent the back projection phase width from being smaller than the minimum width $\pi + 2\pi\gamma_{min}$ [rad].

Namely, the computation device 202 limits the lower limit of the slope width and the lower limit of the back projection phase width, so that the number of back projection views that can be reconstructed can be maintained even at a position apart from the revolution center position. Further, effects of suppressing the artifact caused by motion and the helical artifact that occurs at an end of the projection data range for back projection in the helical scanning can be maintained.

Figure 18:
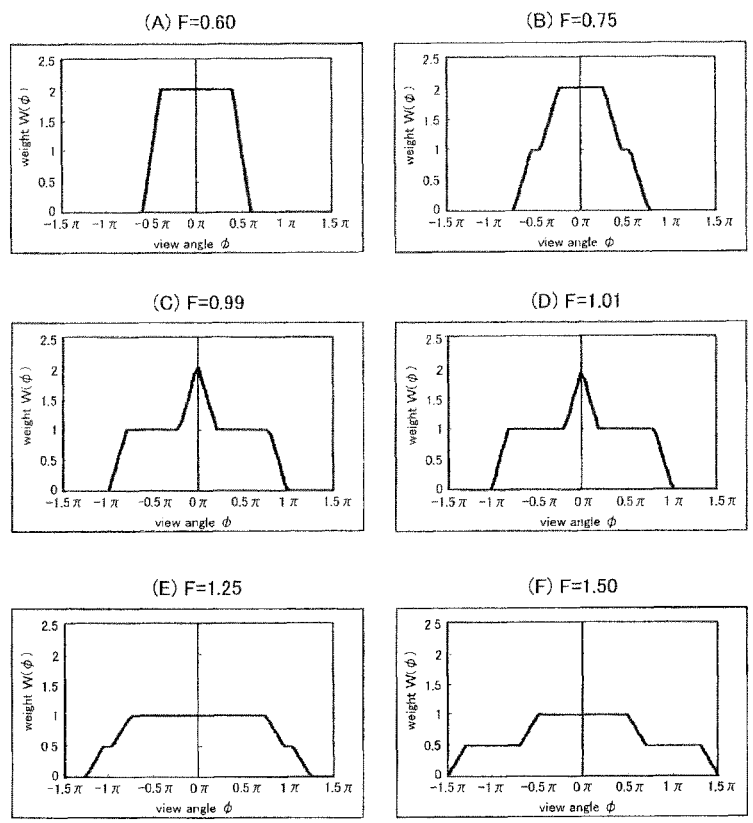
FIG. 18 show examples of weighting functions for parallel beam back projection.

FIG. 18 show weighting functions for parallel beam back projection. The weighting functions illustrated in FIG. 18 are defined by the following equations using N satisfying $2^{N-1} \leq F(R) - \gamma(R) < 2^N$ (N: an integer equal to 0 or larger) in which Ø represents the projection phase of the parallel beam; F, a back projection phase angular width index (the back projection phase width is $2\pi F$[rad] and $F \geq 0.5$); and $\gamma$, the slope width of the view weighting function (the correction angular width is $2\pi\gamma$[rad] and $0 \leq \gamma \leq F-0.5$).

$$Wp(\phi, R) = G \cdot \left\{ Ws\left(\frac{\phi}{2\pi} - \phi_{c1}, \eta, \gamma(R)\right) + Ws\left(\frac{\phi}{2\pi} - \phi_{c2}, \eta, \gamma(R)\right) \right\} \quad (24)$$

$$Ws(\phi, \eta, \gamma) = \begin{cases} 0 & |\phi| \geq \frac{(\eta + \gamma)}{2}, \\ 1 & |\phi| \leq \frac{(\eta - \gamma)}{2}, \\ \frac{1}{\gamma} \cdot \left(\frac{\eta + \gamma}{2} - |\phi|\right) & \text{otherwise,} \end{cases} \quad (25)$$

$$\phi_{c1} = -\frac{\eta + \gamma(R) - F(R)}{2} \quad (26)$$

$$\phi_{c2} = \frac{\eta + \gamma(R) - F(R)}{2} \quad (27)$$

$$\eta = 2^{N-1} \quad (28)$$

$$G = 2^{-N} \quad (29)$$

wherein Wp represents a view weighting function; G, a sub-weight gain; Ws, a sub-weight; Ø, the view phase in the parallel beam; $\emptyset_{c1}$ and $\emptyset_{c2}$, the center view phrases of the sub-weight; $\eta$, a sub-weight reference width; R, a distance from the reference position; $\gamma(R)$, a slope width index at a position apart from the reference position only by R (the correction angular width is $2\pi\gamma(R)$ and $0 \leq \gamma(R) \leq F(R)-0.5$); F(R), a back projection phase width index at a position apart from the reference position by R (the back projection phase width is $2\pi F(R)$ and $F(R) \geq 0.5$); and N, an integer equal to 0 or larger satisfying $2^{N-1} \leq F(R) - \gamma(R) < 2^N$.

The weighting function Wp shown by the equation (24) realizes a weight at an arbitrary back projection phase width of $\pi$ or larger by setting the back projection phase width index F. Further, the weighting function Wp shown by the equation (24) can obtain a constant correction effect (correction of discontinuity at a data end) by setting the slope width $\gamma$ even in the case where the back projection phase width has any value such as $1.3\pi$ or $2\pi$.

Figure 19A:
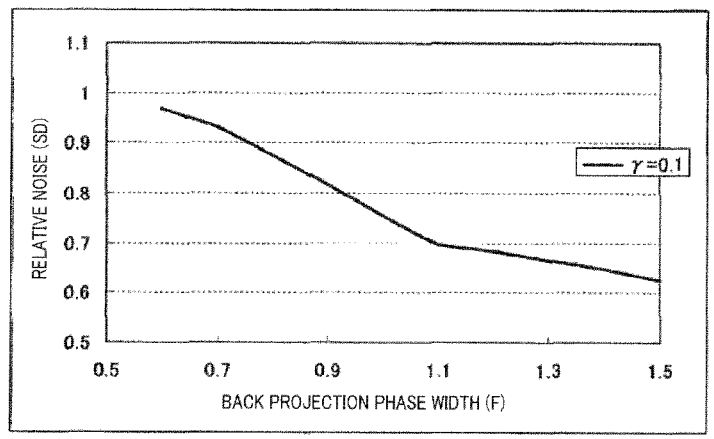
FIG. 19 are diagrams each showing a relation between the back projection phase width and image noise in the view weight.
Figure 19B:
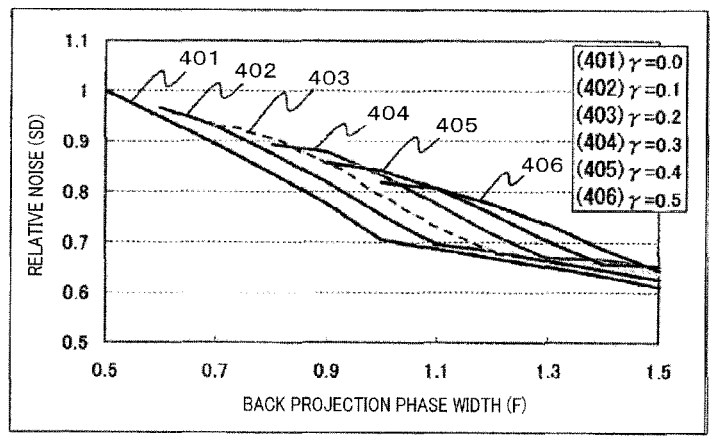

If the weighting function Wp shown by the equation (24) is used, the noise characteristics can be continuously changed while maintaining an arbitrary slope width even in the case where the back projection phase width is changed in accordance with a distance from the reference position, as shown in FIG. 19A and FIG. 19B).

It should be noted that the weighting function Wp shown by the equation (24) changes the weight shapes as shown in FIG. 18A to FIG. 18C using the values of F and $\gamma$ in accordance with R. FIG. 18A shows a case of F<M, FIG. 18B shows a case of M<F<M+$\gamma$/2, and FIG. 18C shows a case of F=M+$\gamma$/2 (an explanation for the shape of the weighting function in the case of F>M+$\gamma$/2 is omitted). In this case, M is $2^N$, and N is an integer equal to 0 or larger satisfying $2^{N-1} \leq F-\gamma < 2^N$.

The weighting functions for fan beam back projection are defined by the following equations using N satisfying $2^{N-1}$F(R)-$\gamma$(R)<$2^N$ (N: an integer equal to 0 or larger) in which 0 represents the projection phase of the parallel beam; F, a back projection phase angular width index (the back projection phase width is $2\pi F$[rad] and $F \geq 0.5$); and $\gamma$, the slope width of the view weighting function (the correction angular width is $2\pi\gamma$[rad] and $0 < \gamma < F-0.5$).

$$Wp(\beta, \alpha) = \quad (30)$$
$$G \cdot \left\{ Ws\left(\frac{\phi}{2\pi} - \beta_{c1} + \alpha, \eta, \gamma(R)\right) + Ws\left(\frac{\phi}{2\pi} - \beta_{c2} + \alpha, \eta, \gamma(R)\right) \right\}$$

$$Ws(\phi, \eta, \gamma(R)) = \begin{cases} 0 & |\phi| \geq \frac{(\eta + \gamma(R))}{2}, \\ 1 & |\phi| \leq \frac{(\eta - \gamma(R))}{2}, \\ \frac{1}{\gamma(R)} \cdot \left(\frac{\eta + \gamma(R)}{2} - |\phi|\right) & \text{otherwise,} \end{cases} \quad (31)$$

$$\phi_{c1} = -\frac{\eta + \gamma(R) - F(R) + 2\alpha}{2} \quad (32)$$

$$\phi_{c2} = \frac{\eta + \gamma(R) - F(R) + 2\alpha}{2} \quad (33)$$

$$\eta = 2^{N-1} \quad (34)$$

$$G = 2^{-N} \quad (35)$$

wherein Wp represents a view weighting function; $\beta$, the projection phase of the fan beam; $\alpha$, a fan angle; G, a sub-weight gain; Ws, a sub-weight; Ø, the projection phase of the parallel beam (the center beam of the fan beam); $\beta_{c1}$ and $\beta_{c2}$, offsets in the phase direction of two sub-view weights (relative view positions from the weight center); $\eta$, a sub-weight reference width; R, a distance from the reference position; $\gamma(R)$, a slope width index at a position apart from the reference position only by R (the correction angular width is $2\pi\gamma(R)$ and $0 \leq \gamma(R) \leq F(R)-0.5$); F(R), a back projection phase width index at a position apart from the reference position by R (the back projection phase width is $2\pi F(R)$ and $F(R) \geq 0.5$); and N, an integer equal to 0 or larger satisfying $2^{N-1} \leq F(R) - \gamma(R) < 2^N$.

If the weighting function Wp shown by the equation (30) is used, the noise characteristics can be continuously changed while maintaining an arbitrary slope width even in the case where the back projection phase width is changed in accordance with a distance from the reference position.

According to the image reconstruction method of the embodiment, more redundant data can be used in both cases of the fan beam and the cone beam without using the weight with the phase width limited as described in Japanese Patent No. 4360817.

EXAMPLE

Next, an example of an image reconstruction method in the embodiment will be described reference to FIG. 20 to FIG. 27. As comparison examples, the back projection phase width is set at a certain value and the smallest value that can be used in an image as in the method of Japanese Patent No. 4360817 (conventional method 1). Further, the back projection phase width is set at a value variable for each pixel and a value that can be used most for the projection data in each pixel as in the method of Japanese Patent No. 4612347 (conventional method 2).

In the conventional method 1, the same back projection phase width was used in all pixels in a maximum FOV of 500 mm. In the conventional method 2, the maximum back projection phase width was calculated in each pixel in a maximum FOV of 500 mm. In the present invention, the rotational center position was used as the reference position, and the back projection phase width in each pixel was calculated so as to have the same value in a concentric manner from the reference position in an axial plane.

As shown in FIG. 20, in the case of a beam pitch of 0.58, the back projection phase width of the conventional method 2 was 1.50 to 2.17, the back projection phase width of the conventional method 1 was 1.50, and the back projection phase width of the present invention was 1.51 to 1.73. When being compared to the back projection phase width of the conventional method 1, the back projection phase width of the present invention was increased by up to about 15%. Namely, the back projection phase width wider than that of the conventional method 1 by up to about 15% was used in the present invention.

As shown in FIG. 21, in the case of a beam pitch of 0.83, the back projection phase width of the conventional method 2 was 0.76 to 1.32, the back projection phase width of the conventional method 1 was 0.75, and the back projection phase width of the present invention was 0.78 to 1.20. When being compared to the back projection phase width of the conventional method 1, the back projection phase width of the present invention was increased by up to about 60%. Namely, the back projection phase width wider than that of the conventional method 1 by up to about 60% was used in the present invention.

As shown in FIG. 22, in the case of a beam pitch of 1.08, the back projection phase width of the conventional method 2 was 0.62 to 1.17, the back projection phase width of the conventional method 1 was 0.65, and the back projection phase width of the present invention was 0.67 to 0.93. When being compared to the back projection phase width of the conventional method 1, the back projection phase width of the present invention was increased by up to about 43%. Namely, the back projection phase width wider than that of the conventional method 1 by up to about 43% was used in the present invention.

Figure 23:
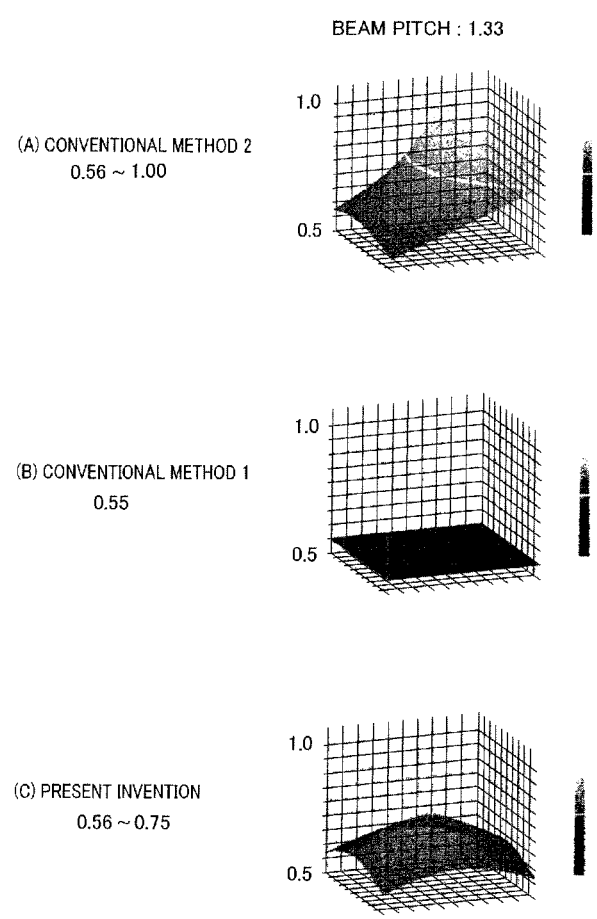
FIG. 23 show calculation results of the back projection phase widths in the case of a beam pitch of 1.33.

As shown in FIG. 23, in the case of a beam pitch of 1.33, the back projection phase width of the conventional method 2 was 0.56 to 1.00, the back projection phase width of the conventional method 1 was 0.55, and the back projection phase width of the present invention was 0.56 to 0.75. When being compared to the back projection phase width of the conventional method 1, the back projection phase width of the present invention was increased by up to about 36%. Namely, the back projection phase width wider than that of the conventional method 1 by up to about 36% was used in the present invention.

As shown in FIG. 24 to FIG. 27, in all cases of beam pitches of 0.58, 0.83, 1.08, and 1.33, unsteady noise irregularities were generated in the conventional method 2. No noise irregularities were generated in the conventional method 1, but noise was increased as a whole. The present invention could regularly control the noise. Specifically, the present invention could eliminate the noise irregularities at the upper, lower, left, and right positions relative to the reference position (rotational center position).

Table 1 shows a comparison result of the amount of noise at the rotational center position.

TABLE 1

| | Beam pitch | 0.58 | 0.83 | 1.08 | 1.33 |
|---|---|---|---|---|---|
| Back projection phase width | Conventional method 1 | 1.50 | 0.75 | 0.65 | 0.55 |
| | Present invention | 1.73 | 1.21 | 0393 | 0.75 |
| Relative noise | Conventional method 1 | 0.91 | 1.29 | 1.34 | 1.39 |
| | Present invention | 0.89 | 0.98 | 1.16 | 1.25 |
| Noise reduction ratio | | 2.8% | 23.9% | 13.6% | 10.2% |
| Radiation exposure reduction effect (corresponding value) | | 5.4% | 42.1% | 25.4% | 19.3% |

As shown in Table 1, in the case of a beam pitch of 0.58, the amount of noise could be reduced by about 2.8% in the present invention as compared to the conventional method 1. Further, in the case of a beam pitch of 0.83, the amount of noise could be reduced by about 23.9% in the present invention as compared to the conventional method 1. Further, in the case of a beam pitch of 1.08, the amount of noise could be reduced by about 13.6% in the present invention as compared to the conventional method 1. Further, in the case of a beam pitch of 1.33, the amount of noise could be reduced by about 10.2% in the present invention as compared to the conventional method 1.

Further, as shown in Table 1, in the case of a beam pitch of 0.58, the radiation exposure reduction effect (corresponding value) was increased by about 5.4% in the present invention as compared to the conventional method 1. Further, in the case of a beam pitch of 0.83, the radiation exposure reduction effect (corresponding value) was increased by about 42.1% in the present invention as compared to the conventional method 1. Further, in the case of a beam pitch of 1.08, the radiation exposure reduction effect (corresponding value) was increased by about 25.4% in the present invention as compared to the conventional method 1. Further, in the case of a beam pitch of 1.33, the radiation exposure reduction effect (corresponding value) was increased by about 19.3% in the present invention as compared to the conventional method 1.

According to the embodiment as described above, the computation device 202 calculates the hack projection phase width in each pixel in accordance with the function of a distance from the reference position regulated by one or more reference points on the axial plane, calculates the view weight using the back projection phase width in each pixel, and reconstructs the CT image using the view weight. Accordingly, it is possible to create a reconstructed image by which an appropriate image diagnosis in accordance with the characteristics of a site (in particular, a bilaterally symmetric site) can be performed.

It is apparent from the above description related to the embodiment that the object of the present invention has been achieved. The present invention has been described and illustrated in detail. However, these are intended for explanation and illustration only, and the present invention is not limited to these. For example, the scan method is not limited to any one of the first generation, second generation, third generation, and fourth generation. Further, for example, the present invention can be applied to a multi-vessel CT with plural X-ray sources mounted, a cathode scan CT, an electron beam CT, and a C-arm CT. Further, for example, the present invention can be applied to any one of a detector arranged on a cylindrical surface about the X-ray source, a planar detector, a detector arranged on a spherical surface about the X-ray source, and a detector arranged on a cylindrical surface about the rotational axis. The gist of the present invention is limited only by the scope of claims.

What is claimed is:

1. An X-ray CT apparatus comprising:
an X-ray generation device including a cathode and anode, to irradiate an X-ray from around a test object;
an X-ray detection device including plural detectors to detect the X-ray penetrating the test object;
a data collection device that collects data detected by the X-ray detection device; and
a computation device that inputs the data collected by the data collection device to create projection data and reconstructs a CT image using the projection data,
wherein the computation device calculates a back projection phase width in each pixel on the basis of a reduction rate of the back projection phase width relative to a reference position regulated by one or more reference points on an axial plane at a position apart from the reference position only by a reference distance, calculates a view weight using the back projection phase width in each pixel, and reconstructs the CT image using the view weight.

2. The X-ray CT apparatus according to claim 1, wherein the computation device calculates the back projection phase width in each pixel in accordance with a function of the distance.

3. The X-ray CT apparatus according to claim 2, wherein the computation device calculates the back projection phase width in each pixel so as to have the same value in a concentric manner from the reference position as a rotational center position in the axial plane.

4. The X-ray CT apparatus according to claim 2, wherein the computation device calculates the back projection phase width in each pixel so as to be monotonically narrowed relative to the distance from the reference position as a test object center position in the axial plane and so as to have the same value in a concentric manner.

5. The X-ray CT apparatus according to claim 1, wherein the computation device calculates the back projection phase width in each pixel so as to be monotonically narrowed relative to the distance from the reference position as a reconstruction center position in the axial plane and so as to have the same value in a concentric manner.

6. The X-ray CT apparatus according to claim 2, wherein the computation device limits a lower limit of a slope width of a view weighting function regulating the view weight and a lower limit of the back projection phase width.

7. The X-ray CT apparatus according to claim 2, wherein the computation device calculates the back projection phase width in each pixel on the basis of the back projection phase width at a preliminarily-set reference position and the back projection phase width at the position apart from the reference position only by the reference distance.

8. The X-ray CT apparatus according to claim 2, wherein the computation device changes a value of a base variable to calculate the back projection phase width in each pixel in accordance with a site.

9. The X-ray CT apparatus according to claim 2, wherein the computation device changes a value of a base variable to calculate the back projection phase width in each pixel in accordance with a reconstruction filter.

10. The X-ray CT apparatus according to claim 2, wherein it is possible to obtain the projection data by axial scanning, and the computation device narrows the back projection phase width in each pixel in accordance with a distance from a reference slice in the body axis direction.

11. An X-ray CT apparatus comprising:
an X-ray generation device including a cathode and anode, to irradiate an X-ray from around a test object;
an X-ray detection device including plural detectors to detect the X-ray penetrating the test object;
a data collection device that collects data detected by the X-ray detection device; and
a computation device that inputs the data collected by the data collection device to create projection data and reconstructs a CT image using the projection data,
wherein the computation device calculates a back projection phase width in each pixel on the basis of a distance from a reference position regulated by one or more reference points on an axial plane, calculates a view weight using the back projection phase width in each pixel, and reconstructs the CT image using the view weight,
wherein the computation device limits a lower limit of a slope width of a view weighting function regulating the view weight and a lower limit of the back projection phase width, and
wherein the lower limit $\gamma_{min}$ of the slope width satisfies $\gamma_{min} \geq 0$, and the lower limit $F_{min}$ of the back projection phase width satisfies $F_{min} \geq 0.5 + \gamma_{min}$.

12. An image reconstruction method in an x-ray CT apparatus which includes an X-ray generation device including a cathode and anode, to irradiate an X-ray from around a test object, an X-ray detection device including plural detectors to detect the X-ray penetrating the test object, a data collection device that collects data detected by the X-ray detection device, and a computation device that inputs the data collected by the data collection device to create projection data and reconstructs a CT image using the projection data, the method comprising the steps executed by the computation device of:
calculating a back projection phase width in each pixel on the basis of a reduction rate of the back projection phase width relative to a reference position regulated by one or more reference points on an axial plane at a position apart from the reference position only by a reference distance, calculating a view weight using the back projection phase width in each pixel, and reconstructing the CT image using the view weight.

13. An X-ray CT apparatus comprising:
an X-ray generation device including a cathode and anode, to irradiate an X-ray from around a test object;
an X-ray detection device including plural detectors to detect the X-ray penetrating the test object;
a data collection device that collects data detected by the X-ray detection device; and
a computation device that inputs the data collected by the data collection device to create projection data and reconstructs a CT image using the projection data,
wherein the computation device calculates a back projection phase width in each pixel on the basis of a distance from a reference position regulated by one or more reference points on an axial plane, calculates a view weight using the back projection phase width in each pixel, and reconstructs the CT image using the view weight, and
wherein the computation device calculates the back projection phase width in each pixel from the reference position other than a rotational center position in the axial plane as to have the same value in a concentric manner from the reference position.

14. The X-ray CT apparatus according to claim 13, wherein the computation device calculates the back projection phase width in each pixel so as to be monotonically narrowed relative to the distance from the reference position as a test object center position in the axial plane.

15. The X-ray CT apparatus according to claim 13, wherein the computation device calculates the back projection phase width in each pixel so as to be monotonically narrowed relative to the distance from the reference position as a reconstruction center position in the axial plane.

* * * * *